US006366860B1

(12) United States Patent
Rozzell, Jr. et al.

(10) Patent No.: US 6,366,860 B1
(45) Date of Patent: Apr. 2, 2002

(54) SYNTHETIC GENES FOR ENHANCED EXPRESSION

(75) Inventors: J. David Rozzell, Jr., Burbank; Peter Bui, El Monte, both of CA (US)

(73) Assignee: Biocatalytics, Inc., Burbank, CA (US)

( * ) Notice: Subject to any disclaimer, the term of this patent is extended or adjusted under 35 U.S.C. 154(b) by 0 days.

(21) Appl. No.: 09/494,921

(22) Filed: Jan. 31, 2000

(51) Int. Cl.⁷ .................. G01N 31/00; G01N 33/48; C07D 267/22; C07D 245/00
(52) U.S. Cl. ............... 702/27; 702/19; 702/30; 702/32; 540/456; 540/460
(58) Field of Search ............... 702/27, 30, 19, 702/32; 540/456, 460

(56) References Cited

U.S. PATENT DOCUMENTS

| | | |
|---|---|---|
| 5,861,154 A | 1/1999 | Soda et al. |
| 5,863,788 A | 1/1999 | Soda et al. |
| 5,891,704 A | 4/1999 | Yuying |

OTHER PUBLICATIONS

Zahn, K., Overexpression of an mRNA Dependent on Rare Codons Inhibits Protein Synthesis and Cell Growth, *Journal of Bacteriology*, May 1996, p 2926–2933.

Kane, J. F., Effects of Rare Codon Clusters on High–Level Expression of Heterologous Proteins in *Escherichia Coli*, Current Opinion in Biotechnology Ltd ISSN, vol. 6 p 494–500.

Nakayama, T. et al., Purification of Bacterial L–Methionine γ–Lyase, Analytical Biochemistry, vol. 138 p 421–424.

*Primary Examiner*—John S. Brusca
*Assistant Examiner*—Young Kim
(74) *Attorney, Agent, or Firm*—Christie, Parker & Hale, LLP

(57) ABSTRACT

A method of making a synthetic nucleic acid sequence comprises providing a starting nucleic acid sequence, which optionally encodes an amino acid sequence, and determining the predicted $\Delta G_{folding}$ of the sequence. The starting nucleic acid sequence can be a naturally occurring sequence or a non-naturally occurring sequence. The starting nucleic acid sequence is modified by replacing at least one codon from the starting nucleic acid sequence with a different corresponding codon to provide a modified nucleic acid sequence. As used herein, a "different corresponding codon" refers to a codon which does not have the identical nucleotide sequence, but which encodes the identical amino acid. The predicted $\Delta G_{folding}$ of the modified nucleic acid sequence is determined and compared with the $\Delta G_{folding}$ of the starting nucleic acid sequence. In accordance with the invention, the predicted $\Delta G_{folding}$ of the starting nucleic acid sequence can be determined before or after the modified starting nucleic acid is provided.

23 Claims, 7 Drawing Sheets

Figure 1A

C atg GGT cac ggc tcc aac aaA ctG ccG ggC ttt gcT acc cgC
gcT atC cac caC ggT taT gac ccG cag gaT cac ggT ggT gca ctg
gtT ccG ccg gtT tac cag acT gcT acT ttc acc ttc ccG acc gtT
gaa tac ggc gct gcg tgc ttt gcT ggc gaA cag gcT ggT caC ttc
tac TCC cgT atc tcc aac ccG acc ctG aac ctg ctg gaa gca cgT
atg gcA tcT ctg gaa ggc ggc gaA gcT ggT ctg gcg ctg gcA tcT
ggT atg ggC gcg atc acC tcT acC ctG tgg acC ctg ctg cgT ccG
ggt gac gaA gtT ctg ctg ggc aac acc ctg taT ggT tgT acT ttt
gcT ttc ctg cac cac ggT atc ggT gaA ttc ggC gtT aaA ctg cgT
caC gtA gaT atg gct gac ctg cag gca ctg gaA gcg gcT atg acC
ccg gcT acc cgT gtT atc taC ttc gaA tcC ccg gcT aac ccG aac
atg cac atg gcT gaC atc gcA ggT gtT gcT aaA atC gcT cgT aag
cac ggc gcT acc gtA gtT gtT gaT aac acc tac tgT acT ccg tac
ctg caA cgT ccG ctg gaA ctg ggc gcT gac ctg gtT gtT caC tcC
gcT acT aaA tac ctg TCC ggc caC ggc gac atc act gct ggc atC
gtA gtA ggc TCC cag gca ctg gtT gac cgt atC cgt ctg caA ggT
ctG aaA gac atg acc ggc gcT gtT ctG tcC ccG caC gac gcA gca
ctg Ctg atg cgT ggT atc aag acc ctG aac ctg cgT atg gac cgT
cac tgT gcT aac gct cag gtA ctg gcT gaA ttc ctG gcT cgT cag
ccg cag gtA gaA ctg atc caC taT ccg ggc ctg gcT TCC ttc ccg
cag tac acT ctg gcA cgT cag cag atg TCC cag ccg ggc ggT atg
atc gcT ttc gaa ctG aag ggT ggc atc ggC gcT ggT cgT cgT ttc
atg aac gcT ctg caG ctg ttc TCC cgT gcg gtT TCC ctg ggT gaC
gcT gaA tcC ctg gcg cag cac ccg gca TCC atg act caC tcc TCC
taC acT ccG gaA gaA cgt gcg caC tac ggc atc tcc gaA ggC ctg
gtT cgT Ctg tcT gtT ggT ctg gaa gac atc gaT gaT ctg ctg gcA
gaC gtT caG cag gcT ctG aag gcT agC gcT tga GGA TCC

Figure 1B

C atg GGT cac ggc tcc aac aaA ctG ccG ggC ttt gcT acc cgC
gcT atC cac caC ggT taT gac ccG cag gaT cac ggT ggT gca ctg
gtT ccG ccg gtT tac cag acT gcT acT ttc acc ttc ccG acc gtT
gaa tac ggc gct gcg tgc ttt gcT ggc gaA cag gcT ggT caC ttc
tac TCC cgT atc tcc aac ccG acc ctG aac ctg ctg gaa gca cgT
atg gcA tcT ctg gaa ggc ggc gaA gcT ggT ctg gcg ctg gcA tcT
ggT atg ggC gcg atc acC tcT acC ctG tgg acC ctg ctg cgT ccG
ggt gac gaA gtT ctg ctg ggc aac acc ctg taT ggT tgT acT ttt
gcT ttc ctg cac cac ggT atc ggT gaA ttc ggC gtT aaA ctg cgT
caC gtA gaT atg gct gac ctg cag

Figure 1C ctg cag gca ctg gaA gcg gcT atg acC ccg gcT acc cgT gtT atc
taC ttc gaA tcC ccg gcT aac ccG aac atg cac atg gcT gaC atc
gcA ggT gtT gcT aaA atC gcT cgT aag cac ggc gcT acc gtA gtT
gtT gaT aac acc tac tgT acT ccg tac ctg caA cgT ccG ctg gaA
ctg ggc gcT gac ctg gtT gtT caC tcC gcT acT aaA tac ctg TCC
ggc caC ggc gac atc act gct ggc atC gtA gtA ggc TCC cag gca
ctg gtT gac cgt atC cgt ctg caA ggT ctG aaA gac atg acc ggc
gcT gtT ctG tcC ccG caC gac gcA gca ctg Ctg atg cgT ggT atc
aag acc ctG aac ctg cgT atg gac cgT cac tgT gcT aac gct cag
gtA ctg gcT gaA

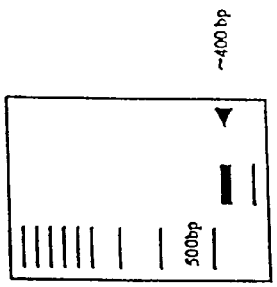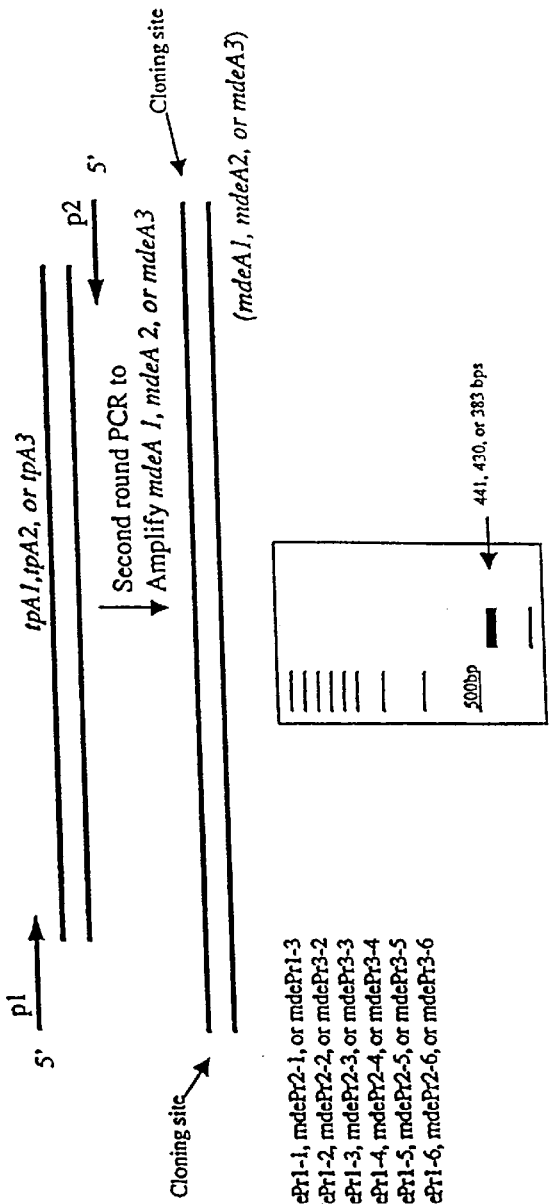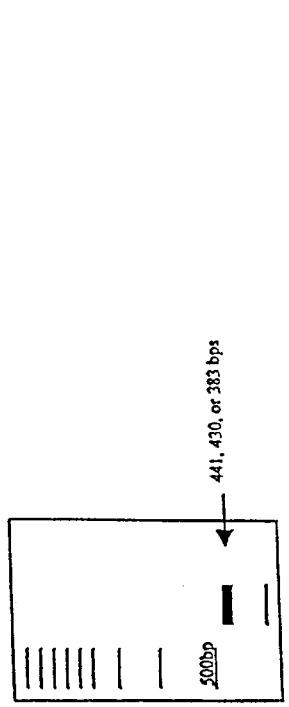
Figure 2A
Figure 2B
P1= mdePr1-1, mdePr2-1, or mdePr3-1
P2= mdePr1-2, mdePr2-2, or mdePr3-2
P3= mdePr1-3, mdePr2-3, or mdePr3-3
P4= mdePr1-4, mdePr2-4, or mdePr3-4
P5= mdePr1-5, mdePr2-5, or mdePr3-5
P6= mdePr1-6, mdePr2-6, or mdePr3-6

Figure 4A: THE INDUCTION OF THE SYNTHETIC *P. putida* METHIONINE -GAMMA-LYASE BL21/pTM
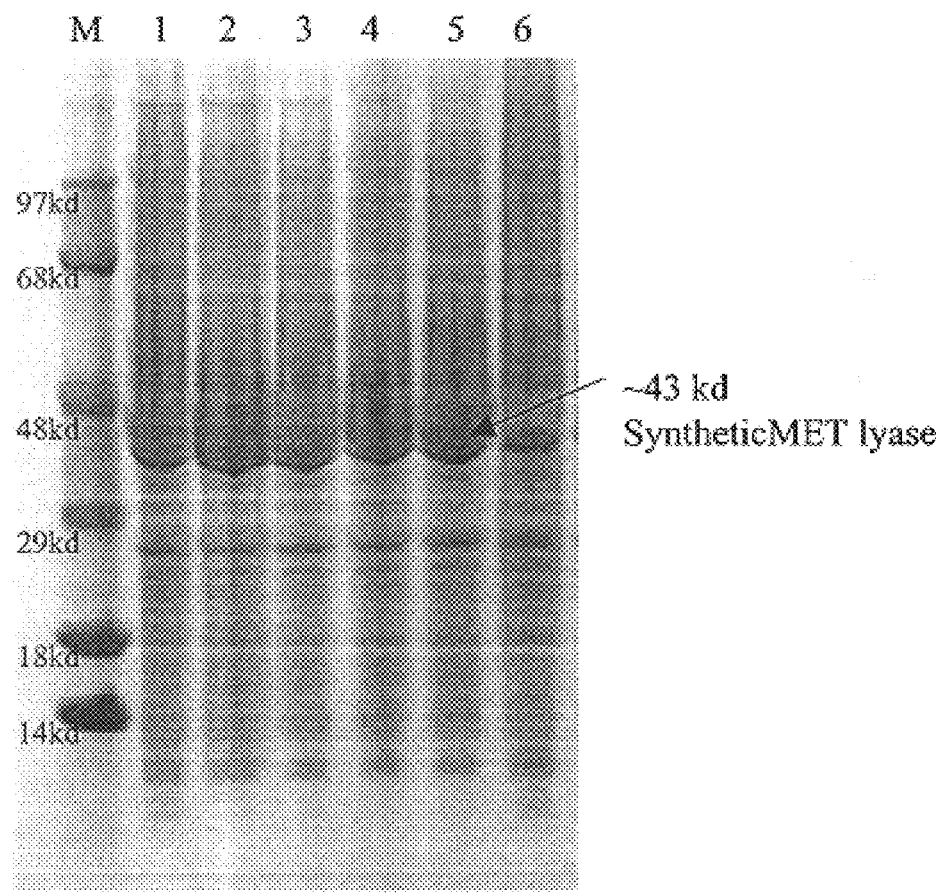

Figure 4B: The induction of native *P. putida* Methionine lyase(pSIT-mdeA)
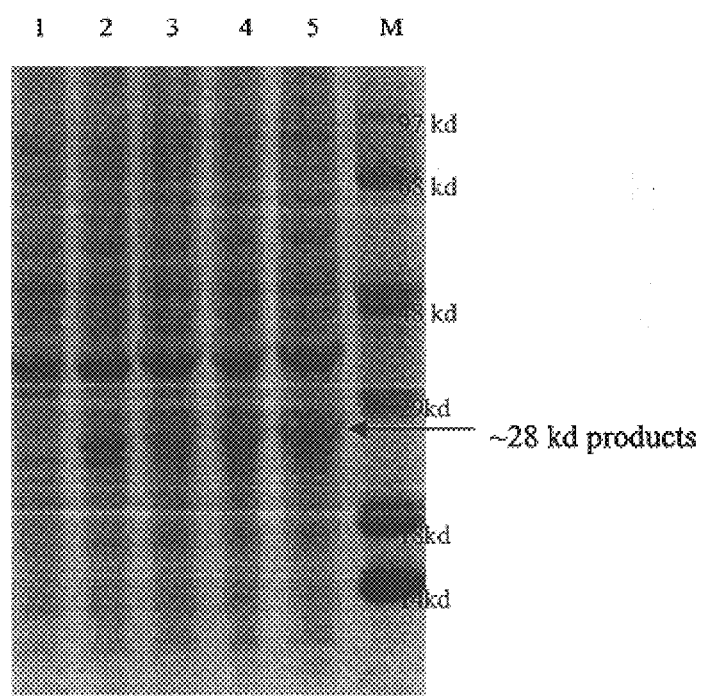

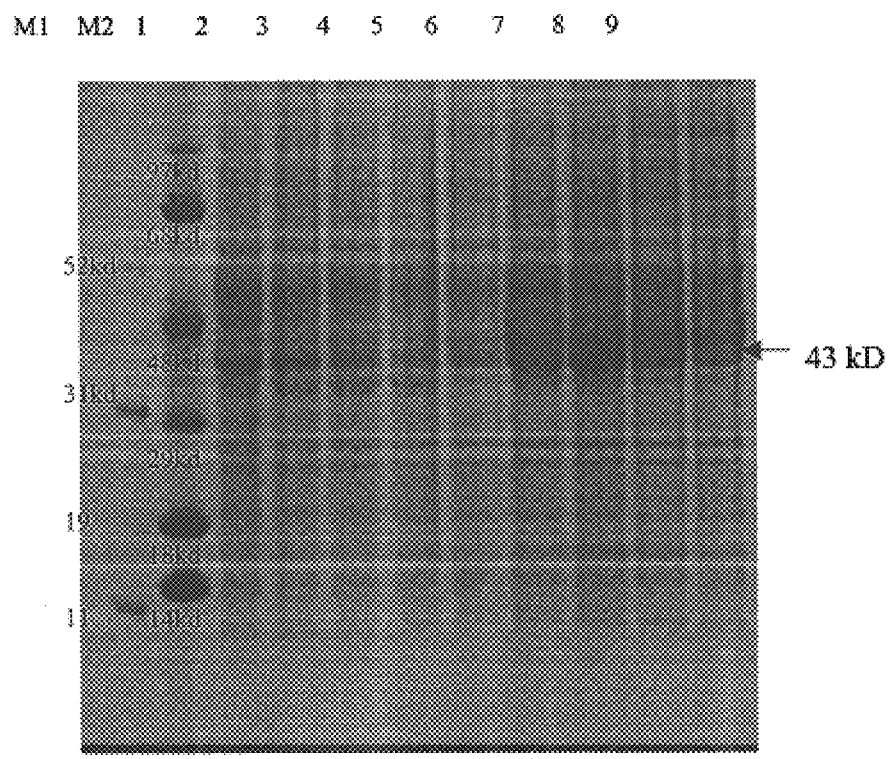
Figure 5: The Induction of the *P. putida Naphthalene* Dioxygenase (NDA) and the *T. vaginalis* methionine -gamma- lyase (*mgl 1*)

SEQUENCE LISTING

```
<160> NUMBER OF SEQ ID NOS: 30

<210> SEQ ID NO 1
<211> LENGTH: 1197
<212> TYPE: DNA
<213> ORGANISM: Pseudomonas putida

<400> SEQUENCE: 1
atgcacggct ccaacaagct cccaggattt gccaccgcg ccattcacca tggctacgac      60
ccccaggacc acggcggcgc actggtgcca ccggtctacc agaccgcgac gttcaccttc     120
cccaccgtgg aatacggcgc tgcgtgcttt gccggcgagc aggccgggca tttctacagc     180
cgcatctcca accccaccct caacctgctg gaagcacgca tggcctcgct ggaaggcggc     240
```

-continued

```
gaggccgggc tggcgctggc ctcgggcatg ggggcgatca cgtccacgct atggacactg      300
ctgcgccccg gtgacgaggt gctgctgggc aacaccctgt acggctgcac ctttgccttc      360
ctgcaccacg gcatcggcga gttcggggtc aagctgcgcc atgtggacat ggccgacctg      420
caggcactgg aggcggccat gacgccggcc acccgggtga tctatttcga gtcgccggcc      480
aaccccaaca tgcacatggc cgatatcgcc ggcgtggcga agattgcacg caagcacggc      540
gcgaccgtgg tggtcgacaa cacctactgc acgccgtacc tgcaacggcc actggagctg      600
ggcgccgacc tggtggtgca ttcggccacc aagtacctga gcggccatgg cgacatcact      660
gctggcattg tggtgggcag ccaggcactg gtggaccgta cgtctgca gggcctcaag       720 gacatgaccg tgcggtgct ctcgccccat gacgccgcac tgttgatgcg cggcatcaag      780
accctcaacc tgcgcatgga ccgccactgc gccaacgctc aggtgctggc cgagttcctc      840
gcccggcagc cgcaggtgga gctgatccat tacccgggcc tggcgagctt ccgcagtac      900 accctggccc gccagcagat gagccagccg ggcggcatga tcgccttcga actcaagggc      960
ggcatcggtg ccgggcggcg gttcatgaac gccctgcaac tgttcagccg cgcggtgagc     1020
ctgggcgatg ccgagtcgct ggcgcagcac ccggcaagca tgactcattc cagctatacc     1080
ccagaggagc gtgcgcatta cggcatctcc gaggggctgg tgcggttgtc ggtggggctg     1140
gaagacatcg cgacctgct ggccgatgtg caacaggcac tcaaggcgag tgcctga       1197
```

<210> SEQ ID NO 2
<211> LENGTH: 399
<212> TYPE: PRT
<213> ORGANISM: Artificial Sequence
<220> FEATURE:
<220> FEATURE:
<223> OTHER INFORMATION: Description of Artificial Sequence: Synthetic
      sequence encoding methionine gamma-lyase derived
      from but not identical to Pseudomonas putida
      methionine gamma-lyase

<400> SEQUENCE: 2

```
Met Gly His Gly Ser Asn Lys Leu Pro Gly Phe Ala Thr Arg Ala Ile
 1               5                  10                  15

His His Gly Tyr Asp Pro Gln Asp His Gly Ala Leu Val Pro Pro
            20                  25                  30

Val Tyr Gln Thr Ala Thr Phe Thr Phe Pro Thr Val Glu Tyr Gly Ala
        35                  40                  45

Ala Cys Phe Ala Gly Glu Gln Ala Gly His Phe Tyr Ser Arg Ile Ser
    50                  55                  60

Asn Pro Thr Leu Asn Leu Leu Glu Ala Arg Met Ala Ser Leu Glu Gly
65                  70                  75                  80

Gly Glu Ala Gly Leu Ala Leu Ala Ser Gly Met Gly Ala Ile Thr Ser
                85                  90                  95

Thr Leu Trp Thr Leu Leu Arg Pro Gly Asp Glu Val Leu Leu Gly Asn
            100                 105                 110

Thr Leu Tyr Gly Cys Thr Phe Ala Phe Leu His His Gly Ile Gly Glu
        115                 120                 125

Phe Gly Val Lys Leu Arg His Val Asp Met Ala Asp Leu Gln Ala Leu
    130                 135                 140

Glu Ala Ala Met Thr Pro Ala Thr Arg Val Ile Tyr Phe Glu Ser Pro
145                 150                 155                 160

Ala Asn Pro Asn Met His Met Ala Asp Ile Ala Gly Val Ala Lys Ile
                165                 170                 175
```

```
Ala Arg Lys His Gly Ala Thr Val Val Asp Asn Thr Tyr Cys Thr
            180                 185                 190

Pro Tyr Leu Gln Arg Pro Leu Glu Leu Gly Ala Asp Leu Val Val His
            195                 200                 205

Ser Ala Thr Lys Tyr Leu Ser Gly His Gly Asp Ile Thr Ala Gly Ile
    210                 215                 220

Val Val Gly Ser Gln Ala Leu Val Asp Arg Ile Arg Leu Gln Gly Leu
225                 230                 235                 240

Lys Asp Met Thr Gly Ala Val Leu Ser Pro His Asp Ala Ala Leu Leu
                245                 250                 255

Met Arg Gly Ile Lys Thr Leu Asn Leu Arg Met Asp Arg His Cys Ala
                260                 265                 270

Asn Ala Gln Val Leu Ala Glu Phe Leu Ala Arg Gln Pro Gln Val Glu
            275                 280                 285

Leu Ile His Tyr Pro Gly Leu Ala Ser Phe Pro Gln Tyr Thr Leu Ala
            290                 295                 300

Arg Gln Gln Met Ser Gln Pro Gly Gly Met Ile Ala Phe Glu Leu Lys
305                 310                 315                 320

Gly Gly Ile Gly Ala Gly Arg Arg Phe Met Asn Ala Leu Gln Leu Phe
                325                 330                 335

Ser Arg Ala Val Ser Leu Gly Asp Ala Glu Ser Leu Ala Gln His Pro
                340                 345                 350

Ala Ser Met Thr His Ser Ser Tyr Thr Pro Glu Glu Arg Ala His Tyr
            355                 360                 365

Gly Ile Ser Glu Gly Leu Val Arg Leu Ser Val Gly Leu Glu Asp Ile
    370                 375                 380

Asp Asp Leu Leu Ala Asp Val Gln Gln Ala Leu Lys Ala Ser Ala
385                 390                 395

<210> SEQ ID NO 3
<211> LENGTH: 1202
<212> TYPE: DNA
<213> ORGANISM: Artificial Sequence
<220> FEATURE:
<220> FEATURE:
<223> OTHER INFORMATION: Description of Artificial Sequence:  Synthetic
      sequence encoding methionine gamma-lyase derived
      from Pseudomonas putida amino acid sequence

<400> SEQUENCE: 3
catgggtcac ggctccaaca aactgccggg ctttgctacc cgcgctatcc accacggtta      60
tgacccgcag gatcacggtg gtgcactggt tccgccggtt taccagactg ctactttcac    120
cttcccgacc gttgaatacg cgctgcgtg ctttgctggc gaacaggctg gtcacttcta    180
ctcccgtatc tccaacccga ccctgaacct gctggaagca cgtatggcat ctctggaagg    240
cggcgaagct ggtctggcgc tggcatctgg tatgggcgcg atcacctcta ccctgtggac    300
cctgctgcgt ccgggtgacg aagttctgct gggcaacacc ctgtatggtt gtactttgc    360 tttcctgcac acggtatcg gtgaattcgg cgttaaactg cgtcacgtag atatggctga    420
cctgcaggca ctggaagcgg ctatgacccc ggctacccgt gttatctact cgaatcccc    480 ggctaacccg aacatgcaca tggctgacat cgcaggtgtt gctaaaatcg ctcgtaagca    540
cggcgctacc gtagttgttg ataacaccta ctgtactccg tacctgcaac gtccgctgga    600
actgggcgct gacctggttg ttcactccgc tactaaatac ctgtccggcc acggcgacat    660
cactgctggc atcgtagtag ctcccaggc actggttgac cgtatccgtc tgcaaggtct    720
```

-continued

| | |
|---|---:|
| gaaagacatg accggcgctg ttctgtcccc gcacgacgca gcactgctga tgcgtggtat | 780 |
| caagaccctg aacctgcgta tggaccgtca ctgtgctaac gctcaggtac tggctgaatt | 840 |
| cctggctcgt cagccgcagg tagaactgat ccactatccg ggcctggctt ccttcccgca | 900 |
| gtacactctg gcacgtcagc agatgtccca gccgggcggt atgatcgctt tcgaactgaa | 960 |
| gggtggcatc ggcgctggtc gtcgtttcat gaacgctctg cagctgttct cccgtgcggt | 1020 |
| ttccctgggt gacgctgaat ccctggcgca gcaccccggca tccatgactc actcctccta | 1080 |
| cactccggaa gaacgtgcgc actacggcat tccgaaggc ctggttcgtc tgtctgttgg | 1140 |
| tctggaagac atcgatgatc tgctggcaga cgttcagcag gctctgaagg ctagcgcttg | 1200 |
| ag | 1202 |

<210> SEQ ID NO 4
<211> LENGTH: 426
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 4

| | |
|---|---:|
| catgggtcac ggctccaaca aactgccggg ctttgctacc cgcgctatcc accacggtta | 60 |
| tgacccgcag gatcacggtg gtgcactggt tccgccggtt taccagactg ctactttcac | 120 |
| cttcccgacc gttgaatacg gcgctgcgtg ctttgctggc gaacaggctg gtcacttcta | 180 |
| ctcccgtatc tccaacccga ccctgaacct gctggaagca cgtatggcat ctctggaagg | 240 |
| cggcgaagct ggtctggcgc tggcatctgg tatgggcgcg atcacctcta ccctgtggac | 300 |
| cctgctgcgt ccgggtgacg aagttctgct gggcaacacc ctgtatggtt gtacttttgc | 360 |
| tttcctgcac cacggtatcg gtgaattcgg cgttaaactg cgtcacgtag atatggctga | 420 |
| cctgca | 426 |

<210> SEQ ID NO 5
<211> LENGTH: 441
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 5

| | |
|---|---:|
| caagaggcca tgggtcacgg ctccaacaaa ctgccgggct tgctacccg cgctatccac | 60 |
| cacggttatg acccgcagga tcacggtggt gcactggttc cgccggttta ccagactgct | 120 |
| actttcacct tcccgaccgt tgaatacggc gctgcgtgct ttgctggcga acaggctggt | 180 |
| cacttctact cccgtatctc caacccgacc ctgaacctgc tggaagcacg tatggcatct | 240 |
| ctggaaggcg gcgaagctgg tctggcgctg gcatctggta tgggcgcgat cacctctacc | 300 |
| ctgtggaccc tgctgcgtcc gggtgacgaa gttctgctgg gcaacaccct gtatggttgt | 360 |
| acttttgctt tcctgcacca cggtatcggt gaattcggcg ttaaactgcg tcacgtagat | 420 |
| atggctgacc tgcaggcact g | 441 |

<210> SEQ ID NO 6
<211> LENGTH: 410

```
<212> TYPE: DNA
<213> ORGANISM: Artificial Sequence
<220> FEATURE:
<220> FEATURE:
<223> OTHER INFORMATION: Description of Artificial Sequence:  Synthetic
      sequence encoding a portion of methionine
      gamma-lyase from Pseudomonas putida

<400> SEQUENCE: 6
ggcactggaa gcggctatga ccccggctac ccgtgttatc tacttcgaat ccccggctaa      60
cccgaacatg cacatggctg acatcgcagg tgttgctaaa atcgctcgta agcacggcgc     120
taccgtagtt gttgataaca cctactgtac tccgtacctg caacgtccgc tggaactggg     180
cgctgacctg gttgttcact ccgctactaa atacctgtcc ggccacggcg acatcactgc     240
tggcatcgta gtaggctccc aggcactggt tgaccgtatc cgtctgcaag gtctgaaaga     300
catgaccggc gctgttctgt ccccgcacga cgcagcactg ctgatgcgtg gtatcaagac     360
cctgaacctg cgtatggacc gtcactgtgc taacgctcag gtactggctg                410

<210> SEQ ID NO 7
<211> LENGTH: 430
<212> TYPE: DNA
<213> ORGANISM: Artificial Sequence
<220> FEATURE:
<220> FEATURE:
<223> OTHER INFORMATION: Description of Artificial Sequence:  Synthetic
      sequence encoding a portion of methionine
      gamma-lyase from Pseudomonas putida

<400> SEQUENCE: 7
gctgacctgc aggcactgga agcggctatg accccggcta cccgtgttat ctacttcgaa      60
tccccggcta cccgaacat gcacatggct gacatcgcag gtgttgctaa atcgctcgt      120 aagcacggcg ctaccgtagt tgttgataac acctactgta ctccgtacct gcaacgtccg     180
ctggaactgg gcgctgacct ggttgttcac tccgctacta aatacctgtc cggccacggc     240
gacatcactg ctggcatcgt agtaggctcc caggcactgg ttgaccgtat ccgtctgcaa     300
ggtctgaaag acatgaccgg cgctgttctg tccccgcacg acgcagcact gctgatgcgt     360
ggtatcaaga ccctgaacct gcgtatggac cgtcactgtg ctaacgctca ggtactggct     420
gaattcctgg                                                            430

<210> SEQ ID NO 8
<211> LENGTH: 366
<212> TYPE: DNA
<213> ORGANISM: Artificial Sequence
<220> FEATURE:
<220> FEATURE:
<223> OTHER INFORMATION: Description of Artificial Sequence:  Synthetic
      sequence encoding a portion of methionine
      gamma-lyase from Pseudomonas putida

<400> SEQUENCE: 8
aattcctggc tcgtcagccg caggtagaac tgatccacta tccgggcctg gcttccttcc      60
cgcagtacac tctggcacgt cagcagatgt cccagccggg cggtatgatc gctttcgaac     120
tgaagggtgg catcggcgct ggtcgtcgtt tcatgaacgc tctgcagctg ttctcccgtg     180
cggtttccct gggtgacgct gaatccctgg cgcagcaccc ggcatccatg actcactcct     240
cctacactcc ggaagaacgt gcgcactacg gcatctccga aggcctggtt cgtctgtctg     300
ttggtctgga agacatcgat gatctgctgg cagacgttca gcaggctctg aaggctagcg     360
cttgag                                                                366
```

<210> SEQ ID NO 9
<211> LENGTH: 383
<212> TYPE: DNA
<213> ORGANISM: Artificial Sequence
<220> FEATURE:
<220> FEATURE:
<223> OTHER INFORMATION: Description of Artificial Sequence: Synthetic sequence encoding a portion of methionine gamma-lyase from Pseudomonas putida

<400> SEQUENCE: 9

```
tcttaatgaa ttcctggctc gtcagccgca ggtagaactg atccactatc cgggcctggc    60
ttccttcccg cagtacactc tggcacgtca gcagatgtcc cagccgggcg gtatgatcgc   120
tttcgaactg aagggtggca tcggcgctgg tcgtcgtttc atgaacgctc tgcagctgtt   180
ctcccgtgcg gtttccctgg gtgacgctga atccctggcg cagcacccgg catccatgac   240
tcactcctcc tacactccgg aagaacgtgc gcactacggc atctccgaag gcctggttcg   300
tctgtctgtt ggtctggaag acatcgatga tctgctggca gacgttcagc aggctctgaa   360
ggctagcgct tgaggatcca cca                                            383
```

<210> SEQ ID NO 10
<211> LENGTH: 33
<212> TYPE: DNA
<213> ORGANISM: Artificial Sequence
<220> FEATURE:
<220> FEATURE:
<223> OTHER INFORMATION: Description of Artificial Sequence: Synthetic sequence encoding a portion of methionine gamma-lyase derived from Pseudomonas putida

<400> SEQUENCE: 10

```
caagaggcca tgggtcacgg ctccaacaaa ctg                                  33
```

<210> SEQ ID NO 11
<211> LENGTH: 114
<212> TYPE: DNA
<213> ORGANISM: Artificial Sequence
<220> FEATURE:
<220> FEATURE:
<223> OTHER INFORMATION: Description of Artificial Sequence: Synthetic sequence encoding a portion of methionine gamma-lyase from Pseudomonas putida

<400> SEQUENCE: 11

```
cacggctcca acaaactgcc gggctttgct acccgcgcta tccaccacgg ttatgacccg    60
caggatcacg gtggtgcact ggttccgccg gtttaccaga ctgctacttt cacc          114
```

<210> SEQ ID NO 12
<211> LENGTH: 116
<212> TYPE: DNA
<213> ORGANISM: Artificial Sequence
<220> FEATURE:
<220> FEATURE:
<223> OTHER INFORMATION: Description of Artificial Sequence: Synthetic sequence encoding a portion of methionine gamma-lyase from Pseudomonas putida

<400> SEQUENCE: 12

```
gcttccagca ggttcagggt cgggttggag atacgggagt agaagtgacc agcctgttcg    60
ccagcaaagc acgcagcgcc gtattcaacg gtcgggaagg tgaaagtagc agtctg       116
```

<210> SEQ ID NO 13
<211> LENGTH: 117
<212> TYPE: DNA

<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 13
ctgaacctgc tggaagcacg tatggcatct ctggaaggcg gcgaagctgg tctggcgctg        60
gcatctggta tgggcgcgat cacctctacc ctgtggaccc tgctgcgtcc gggtgac          117

<210> SEQ ID NO 14
<211> LENGTH: 116
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase from Pseudomonas putida

<400> SEQUENCE: 14
gccatatcta cgtgacgcag tttaacgccg aattcaccga taccgtggtg caggaaagca        60
aaagtacaac catacagggt gttgcccagc agaacttcgt cacccggacg cagcag          116

<210> SEQ ID NO 15
<211> LENGTH: 33
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 15
cagtgcctgc aggtcagcca tatctacgtg acg                                      33

<210> SEQ ID NO 16
<211> LENGTH: 33
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 16
gctgacctgc aggcactgga agcggctatg acc                                      33

<210> SEQ ID NO 17
<211> LENGTH: 114
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 17
ctggaggctg ctatgacccc ggctacccgt gttatctact tcgaatcccc ggctaacccg        60
aacatgcaca tggctgacat cgcaggtgtt gctaaaatcg ctcgtaagca cggc             114

<210> SEQ ID NO 18
<211> LENGTH: 115
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 18
ggtatttagt agcggagtga acaaccaggt cagcgcccag ttccagcgga cgttgcaggt     60
acggagtaca gtaggtgtta tcaacaacta cggtagcgcc gtgcttacga gcgat        115

<210> SEQ ID NO 19
<211> LENGTH: 111
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 19
cactccgcta ctaaatacct gtccggccac ggcgacatca ctgctggcat cgtagtaggc     60
tcccaggcac tggttgaccg tatccgtctg caaggtctga agacatgac c              111

<210> SEQ ID NO 20
<211> LENGTH: 115
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 20
gtacctgagc gttagcacag tgacggtcca tacgcaggtt cagggtcttg ataccacgca     60
tcagcagtgc tgcgtcgtgc ggggacagaa cagcgccggt catgtctttc agacc        115

<210> SEQ ID NO 21
<211> LENGTH: 33
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 21
ccaggaattc agccagtacc tgagcgttag cac                                  33

<210> SEQ ID NO 22
<211> LENGTH: 31
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 22
tcttaatgaa ttcctggctc gtcagccgca g                                    31

<210> SEQ ID NO 23
<211> LENGTH: 105
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 23
ctggctcgtc agccgcaggt agaactgatc cactatccgg gcctggcttc cttcccgcag      60
tacactctgg cacgtcagca gatgtcccag ccgggcggta tgatc                    105

<210> SEQ ID NO 24
<211> LENGTH: 106
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 24
cgtcacccag ggaaaccgca cgggagaaca gctgcagagc gttcatgaaa cgacgaccag      60
cgccgatgcc acccttcagt tcgaaagcga tcatgccacc cggctg                   106

<210> SEQ ID NO 25
<211> LENGTH: 106
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 25
gcggtttccc tgggtgacgc tgaatccctg gcgcagcacc cggcatccat gactcactcc      60
tcctacactc cggaagaacg tgcgcactac ggcatctccg aaggcc                   106

<210> SEQ ID NO 26
<211> LENGTH: 98
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida

<400> SEQUENCE: 26
caagcgctag ccttcagagc ctgctgaacg tctgccagca gatcatcgat gtcttccaga      60
ccaacagaca gacgaaccag gccttcggag atgccgta                             98

<210> SEQ ID NO 27
<211> LENGTH: 32
<212> TYPE: DNA
<213> ORGANISM: Artificial Sequence
<220> FEATURE:
<220> FEATURE:
<223> OTHER INFORMATION: Description of Artificial Sequence: Synthetic
      sequence encoding a portion of methionine
      gamma-lyase derived from Pseudomonas putida -continued

<400> SEQUENCE: 27
tggtggatcc tcaagcgcta gccttcagag cc                                    32

<210> SEQ ID NO 28
<211> LENGTH: 1197
<212> TYPE: DNA
<213> ORGANISM: Artificial Sequence
<220> FEATURE:
<223> OTHER INFORMATION: Description of Artificial Sequence:  Synthetic
      sequence encoding methionine gamma-lyase from
      Pseudomonas putida.  Rare arginine codons in E.
      coli  replaced.

<400> SEQUENCE: 28
atgcacggct ccaacaagct cccaggattt gccacccgcg ccattcacca tggctacgac      60
ccccaggacc acgcggcgc actggtgcca ccggtctacc agaccgcgac gttcaccttc     120
cccaccgtgg aatacggcgc tgcgtgcttt gccggcgagc aggccgggca tttctacagc    180
cgcatctcca accccaccct caacctgctg gaagcacgca tggcctcgct ggaaggcggc    240
gaggccgggc tggcgctggc ctcgggcatg ggggcgatca cgtccacgct atggacactg    300
ctgcgccccg gtgacgaggt gctgctgggc aacaccctgt acggctgcac ctttgccttc    360
ctgcaccacg gcatcggcga gttcggggtc aagctgcgcc atgtggacat ggccgacctg    420
caggcactgg aggcggccat gacgccggcc accgtgtga tctatttcga gtcgccggcc     480 aacccccaaca tgcacatggc cgatatcgcc ggcgtggcga agattgcacg caagcacggc    540
gcgaccgtgg tggtcgacaa cacctactgc acgccgtacc tgcaacgtcc actggagctg    600
ggcgccgacc tggtggtgca ttcggccacc aagtacctga gcggccatgg cgacatcact    660
gctggcattg tggtgggcag ccaggcactg gtggaccgta cgtctgca gggcctcaag      720 gacatgaccg gtgcggtgct ctcgccccat gacgccgcac tgttgatgcg cggcatcaag    780
accctcaacc tgcgcatgga ccgccactgc gccaacgctc aggtgctggc cgagttcctc    840
gcccgtcagc gcaggtgga gctgatccat tacccgggcc tggcgagctt cccgcagtac     900
accctggccc gccagcagat gagccagccg gcggcatga tcgccttcga actcaagggc     960
ggcatcggtg ccgggcgtcg tttcatgaac gccctgcaac tgttcagccg cgcggtgagc    1020
ctgggcgatg ccgagtcgct ggcgcagcac ccggcaagca tgactcattc cagctatacc    1080
ccagaggagc gtgcgcatta cggcatctcc gaggggctgg tgcgtttgtc ggtggggctg    1140
gaagacatcg cgacctgct ggccgatgtg caacaggcac tcaaggcgag tgcctga       1197

<210> SEQ ID NO 29
<211> LENGTH: 1197
<212> TYPE: DNA
<213> ORGANISM: Artificial Sequence
<220> FEATURE:
<223> OTHER INFORMATION: Description of Artificial Sequence:  Synthetic
      sequence encoding methionine gamma-lyase from
      Pseudomonas putida.  Rare E. coli codons replaced.

<400> SEQUENCE: 29
atgcacggct ccaacaagct cccaggattt gccacccgcg ccattcacca tggctacgac      60
ccgcaggacc acgcggcgc actggtgcca ccggtctacc agaccgcgac gttcaccttc     120
ccgaccgtgg aatacggcgc tgcgtgcttt gccggcgagc aggccgggca tttctacagc    180
cgcatctcca acccgaccct caacctgctg gaagcacgca tggcctcgct ggaaggcggc    240
gaggccgggc tggcgctggc ctcgggcatg ggggcgatca cgtccacgct gtggacactg    300

-continued

```
ctgcgcccgg gtgacgaggt gctgctgggc aacaccctgt acggctgcac ctttgccttc      360
ctgcaccacg gcatcggcga gttcggggtc aagctgcgcc atgtggacat ggccgacctg      420
caggcactgg aggcggccat gacgccggcc acccgtgtga tctatttcga gtcgccggcc      480
aacccgaaca tgcacatggc cgatatcgcc ggcgtggcga agattgcacg caagcacggc      540
gcgaccgtgg tggtcgacaa cacctactgc acgccgtacc tgcaacgtcc actggagctg      600
ggcgccgacc tggtggtgca ttcggccacc aagtacctga gcggccatgg cgacatcact      660
gctggcattg tggtgggcag ccaggcactg gtggaccgta tccgtctgca gggcctcaag      720
gacatgaccg gtgcggtgct ctcgccgcat gacgccgcac tgttgatgcg cggcatcaag      780
accctcaacc tgcgcatgga ccgccactgc gccaacgctc aggtgctggc cgagttcctc      840
gcccgtcagc cgcaggtgga gctgatccat tacccgggcc tggcgagctt cccgcagtac      900
accctggccc gccagcagat gagccagccg ggcggcatga tcgccttcga actcaagggc      960
ggcatcggtg ccgggcgtcg tttcatgaac gccctgcaac tgttcagccg cgcggtgagc     1020
ctgggcgatg ccgagtcgct ggcgcagcac ccggcaagca tgactcattc cagctatacc     1080
ccagaggagc gtgcgcatta cggcatctcc gagggggctgg tgcgtttgtc ggtggggctg     1140
gaagacatcg acgacctgct ggccgatgtg caacaggcac tcaaggcgag tgcctga        1197
```

<210> SEQ ID NO 30
<211> LENGTH: 1200
<212> TYPE: DNA
<213> ORGANISM: Artificial Sequence
<220> FEATURE:
<223> OTHER INFORMATION: Description of Artificial Sequence: Synthetic
      sequence encoding methionine gamma-lyase derived
      from Pseudomonas putida amino acid sequence.
      Common E. coli codons used.

<400> SEQUENCE: 30

```
atgggtcacg gctccaacaa actgccgggt tttgctaccc gtgctatcca ccacggctac       60
gacccgcagg accacggcgg cgcactggtt ccgccggttt accagaccgc gaccttcacc      120
ttcccgaccg ttgaatacgg cgctgcgtgc tttgctggcg aacaggctgg tcacttctac      180
tcccgtatct ccaacccgac cctgaacctg ctggaagcac gtatggcttc cctggaaggc      240
ggcgaagctg gtctggcgct ggcttccggc atgggtgcga tcacctccac cctgtggacc      300
ctgctgcgtc cgggtgacga agttctgctg ggcaacaccc tgtacggctg caccttcgct      360
ttcctgcacc acggcatcgg cgaattcggt gttaagctgc gtcacgttga catggctgac      420
ctgcaggcac tggaagcggc tatgaccccc gctacccgtg ttatctactt cgaatccccg      480
gctaacccga acatgcacat ggctgaaatc gctggcgttg cgaagatcgc acgtaagcac      540
ggcgcgaccg ttgttgttga caacacctac tgcaccccgt acctgcaacg tccgctggaa      600
ctgggcgctg acctggttgt tcactccgct accaagtacc tgtccggcca cggcgacatc      660
actgctggca tcgttgttgg ctcccaggca ctggttgacc gtatccgtct gcaaggcctg      720
aaggacatga ccggtgcggt tctgtccccg cacgacgctg cactgctgat gcgtggcatc      780
aagcccctga acctgcgtat ggaccgtcac tgcgctaacg ctcaggttct ggctgaattc      840
ctggctcgtc agccgcaggt tgaactgatc cactacccgg gcctggcgtc cttcccgcag      900
tacaccctgg ctcgtcagca gatgtcccag ccgggcggca tgatcgcttt cgaactgaag      960
ggcggcatcg gtgctggtcg tcgtttcatg aacgctctgc agctgttctc ccgtgcggtt     1020
tccctgggcg aagctgaatc cctggcgcag cacccggcat ccatgactca ctcctcctac     1080
```

-continued

```
accccggaag aacgtgcgca ctacggcatc tccgaaggtc tggttcgtct gtccgttggt    1140
ctggaagaca tcgacgacct gctggctgaa gttcagcagg cactgaaggc gagtgcttga    1200
```

SYNTHETIC GENES FOR ENHANCED EXPRESSION

STATEMENT REGARDING FEDERALLY SPONSORED RESEARCH OR DEVELOPMENT

This invention was made with government support under Grant # 1R43DK55951-01 awarded by the National Institutes of Health. The government has certain rights in the invention.

BACKGROUND OF THE INVENTION

The field of the invention is synthetic nucleic acid sequences for improved amplification and expression in a host organism, and methods of creating them.

It has been a goal of biotechnology to promote the expression of cloned genes for analysis of gene structure and function and also for commercial-scale synthesis of desirable gene products. DNA cloning methods have enabled the genetic modification of bacteria and unicellular eukaryotes to produce heterologous gene products. In principle, the genes may originate from almost any source, including other bacteria, animal cells or plant cells. Although this expression of heterologous genes is a function of a variety of complex factors, maximizing the expression of cloned sequences has been under intense and rapid development. Plasmid and viral vectors have been developed in both prokaryotes and eukaryotes that enhance the level of expression of cloned genes. In some cases the vector itself contains the regulatory elements controlling the expression of genes which are not normally expressed in the host cell so that a high level of expression of heterologous genes can be obtained.

Several problems exist, however, in the expression of many proteins across phyla and even across species. Post-translational handling and modification of expressed proteins by the host cell often does not mimic that of the heterologous gene's own cell type. Frequently, even if the protein is expressed in a useful form, heterologous genes are poorly expressed. Low yields of expressed protein may make manufacture of commercially useful quantities impossible or prohibitively costly. Vectors designed to enhance expression are not able to overcome some expression problems if the regulatory elements of the vector are not the constraint on robust expression. Other cellular or translational constraints are at issue.

Genes encoding poorly expressed proteins are often themselves difficult to clone and amplify as well. This is due to secondary structure inherent in the gene, for example caused by high G-C content. Some methods have been used to reduce these difficulties, such as the use of DMSO or betaine to bring G-C and A-T melting behaviors more into alignment, or the use of ammonium sulfate (hydrogen binding cations) to destabilize G-C bonding during PCR. The problem with these methods is that the effects of the additives are concentration dependent, so variations in template size and G-C content mean lengthy optimization procedures. Additionally, these steps do nothing to facilitate subsequent expression of the nucleic acid once it has been cloned.

The frequency of particular codon usage in *Escherichia coli* and other enteric bacteria has long been known, and it has been hypothesized that replacement of certain rare codons encoding a particular amino acid in a heterologous gene with a codon that is more commonly used by such bacteria would enhance expression (see, e.g., Kane, *Curr Opin Biotechnol* 6:494–500 (1995) and Zahn, *J. Bacteriol.*, 178:2926–2933 (1996)). This is based on the theory that rare codons have only a few tRNAs per cell and that transcription of heterologous sequences having numerous occurrences of these rare codons is limited by too few available tRNAs for those codons. However, simple replacement of rare codons does not reliably improve expression of heterologous genes, and no broadly applicable method exists to select which codon changes are best to increase expression of heterologous sequences. Further, it is not known in detail how codon usage is related to expression level.

Bacterial gene products are commonly used as research and assay reagents, and various microbial enzymes increasingly are finding applications as industrial catalysts (see, for example, Rozzell, J. D., "Commercial Scale Biocatalysis: Myths and Realities," *Bioorganic and Medicinal Chemistry*, 7:2253–2261 (1999), herein incorporated by reference). Some have substantial commercial value. Examples include heat-stable Taq polymerase from *Thermus aquaticus*, restriction enzymes such as Eco RI from *E. coli*, lipase from *Pseudomonas cepacia*, β-amylase from Bacillus sp., penicillin amidase from *E. coil* and Bacillus sp., glucose isomerase from the genus Streptomyces, and dehalogenase from *Pseudomonas putida*. Genes from bacteria may express easily in commercially useful host strains, but many do not. In particular, genes from bacteria having significantly different codon preferences from enteric bacteria, including but not limited to filamentous bacteria such as streptomycetes and various strains of the genus Bacillus, Pseudomonas, and the like can be difficult to express abundantly in enteric bacteria such as *E. coli*. An example of a Pseudomonas gene that is difficult to express in *E. coli* is the enzyme methionine gamma-lyase, useful for the assay of L-homocysteine and/or L-methionine as described in U.S. Pat. No. 5,885,767 (herein incorporated by reference). This assay is particularly useful in the diagnosis and treatment of homocystinuria, a serious genetic disorder characterized by an accumulation of elevated levels of L-homocysteine, L-methionine and metabolites of L-homocysteine in the blood and urine. Homocystinuria is more fully described in Mudd et al., "Disorders of transsulfuration," In: Scriver et al., eds., *The Metabolic and Molecular Basis of Inherited Disease*, McGraw-Hill Co., New York, 7$^{th}$ Edition, 1995, pp. 1279–1327 (herein incorporated by reference). In developing an assay for the accurate quantitation of L-homocysteine and L-methionine according to the methods described in U.S. Pat. No. 5,885,767, obtaining large amounts of methionine gamma-lyase is necessary. However, this Pseudomonas gene contains a number of codons that are less commonly found in genes of desirable bacterial hosts for expression such as *E. coli*.

Because plasmid vectors designed to enhance expression with a variety of promotors or other regulatory elements often do not resolve the difficulty in expressing certain genes, and because no systematic approach exists for codon replacement to aid amplification of nucleic acids or their expression, there is clearly a need for an improved method for amplification and expression of genes, including genes from various bacteria such as streptomycetes, Bacillus, Pseudomonas and the like introduced into enteric bacterial hosts such as *E. coli*.

SUMMARY OF THE INVENTION

In one embodiment, the invention is directed to a method of making a synthetic nucleic acid sequence. The method comprises providing a starting nucleic acid sequence, which optionally encodes an amino acid sequence, and determining the predicted $\Delta G_{folding}$ of the sequence. The starting nucleic acid sequence can be a naturally occurring sequence or a non-naturally occurring sequence. The starting nucleic acid sequence is modified by replacing at least one codon from the starting nucleic acid sequence with a different corresponding codon to provide a modified nucleic acid sequence. As used herein, "codon" generally refers to a nucleotide triplet which codes for an amino acid or translational signal (e.g., a stop codon), but can also mean a nucleotide triplet which does not encode an amino acid, as would be the case if the synthetic or modified nucleic acid sequence does not encode a protein (e.g., upstream regulatory elements, signaling sequences such as promotors, etc.). As used herein, a "different corresponding codon" refers to a codon which does not have the identical nucleotide sequence, but which encodes the identical amino acid. The predicted $\Delta G_{folding}$ of the modified nucleic acid sequence is determined and compared with the $\Delta G_{folding}$ of the starting nucleic acid sequence. In accordance with the invention, the predicted $\Delta G_{folding}$ of the starting nucleic acid sequence can be determined before or after the modified starting nucleic acid is provided.

Thereafter, it is determined whether the $\Delta G_{folding}$ of the modified nucleic acid sequence is increased relative to the $\Delta G_{folding}$ of the starting nucleic acid sequence by a desired amount, such as at least about 2%, at least about 10%, at least about 20%, or at least about 30%. If the $\Delta G_{folding}$ of the modified nucleic acid sequence is not increased by the desired amount, the modified nucleic acid sequence is further modified by replacing at least one codon from the modified nucleic acid sequence with a different corresponding codon to provide a different modified nucleic acid sequence. These steps are repeated until the $\Delta G_{folding}$ of the modified nucleic acid sequence is increased by the desired amount to ultimately provide a final nucleic acid sequence, which is the desired nucleic acid sequence.

The modified and/or final nucleic acid sequence can then be physically created. By the present invention, a desired nucleic acid sequence can be created that is more highly expressed in a selected host, such as E. coli, than the starting sequence. By "more highly expressed" is meant more protein product is produced by the same host than would be with the starting sequence, preferably at least 5% more, more prefererably at least 10% more, and most preferably at least 20% more.

Preferably the codon replacement is in a region of the starting nucleic acid sequence or modified nucleic acid sequence containing secondary structure. It is also preferred that the different corresponding codon is one that occurs with higher frequency in the selected host. In a particularly preferred embodiment, the desired amino acid sequence is expressed in Escherichia coli, and the amino acid sequence is from a bacterium of the genus Pseudomonas, and the different corresponding codon is selected to be one that occurs with higher frequency in Escherichia coli than does the replaced codon. Alternatively, or in addition, the different corresponding codon is selected as one that has fewer guanine or cytosine residues than the replaced codon.

In a particularly preferred embodiment, the starting nucleic acid sequence is derived, e.g., converted, from an amino acid sequence native to an organism different from the desired host for expression, for example Pseudomonas.

The method of the invention also provides a modified, final sequence that is more amplifiable than the starting sequence. In other words, the final sequence is amplified more readily in a full length form, more rapidly or in greater quantity.

In another embodiment, the invention is directed to a synthetic nucleic acid sequence having a plurality of codons and encoding a methionine gamma-lyase protein from Pseudomonas putida. As used herein, the phrase "nucleic acid sequence encoding a protein" means that the nucleic acid sequence encodes at least the functional domain of the protein. The sequence having no more than about 95% homology, preferably no more than about 90% homology, more preferably no more than about 85% homology, still more preferably no more than about 80% homology, to a naturally occurring methionine gamma-lyase gene from Pseudomonas putida. At least about 5%, preferably at least about 10%, more preferably at least about 20%, still more preferably at least about 30%, even more preferably at least about 40%, of the codons in the synthetic nucleic acid sequence are different from codons found in the naturally occurring gene.

In one aspect, the codons in the synthetic nucleic acid sequence encode the same amino acids as the codons in the naturally occurring gene. In another aspect, at least one of the codons in the synthetic nucleic acid sequence encodes an amino acid different from the numerically corresponding amino acid found in the naturally occurring sequence. In yet another aspect, at least one of the different codons in the synthetic nucleic acid sequence is in an area of secondary structure in the naturally occurring gene.

In another embodiment, the invention is directed to a method of creating a synthetic nucleic acid. The method comprises providing a sense nucleic acid sequence having a 5' end and a 3' end and providing an antisense nucleic acid sequence having a 5' end and a 3' end. Preferably the sense and antisense nucleic acid sequences are between about 10 and about 200 bases, more preferably between about 80 and about 120 bases. The 3' end of the sense sequence has a plurality of bases complimentary to a plurality of bases of the 3' end of the antisense sequence, thereby forming an area of overlap. Preferably the area of overlap is at least 6 bases, more preferably at least 10 bases, still more preferably at least 15 bases. The 5' end of the sense sequence extends beyond the 3' end of the antisense sequence, and the 5' end of the antisense sequence extends beyond the 3' end of the sense sequence. The method further comprises annealing the sense and antisense sequences at the area of overlap. A polymerase and free nucleotides are added to the sequences. Said nucleotides may be naturally occurring, i.e., A, T, C, G, or U, or they may be non-natural, e.g., iso-cytosine, iso-guanine, xanthine, and the like. The sequences can be annealed before or after addition of the polymerase and free nucleotides. The sequences are extended, wherein the area of overlap serves to prime the extension of the sense and antisense sequences in the 3' direction, forming a double stranded product. The extended sequence can then be amplified. Further, a second step to the method can be added where the double stranded first extension product is separated into an extended sense strand and an extended antisense strand and a second set of sense and antisense nucleic acid sequences are provided having a 5' end and a 3' end. Each has a plurality of bases on its 3' end complementary to a plurality of bases on the 3' end of the extended sense or antisense strand respectively, thereby forming second and third areas of overlap. A polymerase and free nucleotides are added to the sequences and separated strands, wherein the second and third areas of overlap serve to prime a second extension of the sequences and strands that encompasses the sequence of the first sense and antisense nucleic acid sequences and the second sense and antisense nucleic acid sequences.

DESCRIPTION OF THE DRAWINGS

These and other features and advantages of the present invention will be better understood by reference to the following detailed description when considered in conjunction with the accompanying figures wherein:

FIG. 1A: DNA sequence of synthetic mdeA gene (1200 bps with GGT insertion), called synmdeA. Nco I and BamH I cloning sites are engineered at 5' end and 3' end. The bold face uppercase nucleotides are the changed nucleotides from the original mdeA gene sequence.

FIG. 1B: First DNA segment, mdeA1 (426 bps), with Nco I and Pst I cloning sites.

FIG. 1C: Second segment, mdeA2 (414 bps), with Pst I and EcoR I cloning sites.

FIG. 1D: Third segment, mdeA3 (367 bps), with EcoR I and BamH I cloning sites.

FIG. 2A: First round of amplification using long oligonucleotides to generate template (tpA1, tpA2, or tpA3) DNA for each of the three synmdeA segments mdeA1, mdeA2 or mdeA3. PCR amplification relies on overlapping sections of each oligonucleotide, which serves to prime the extension of the neighboring segment.

FIG. 2B: Second round of amplification using the two short oligonucleotides to amplify the full-length segments, mdeA1, mdeA2 or mdeA3. The short oligonucleotides overlap with the 5' ends of the sense and antisense strands to form a template primed by the tpA1, tpA2, or tpA3 strands, resulting in the filling in of both 5' and 3' ends of mdeA1, mdeA2 and mdeA3 after the second round of PCR.

FIG. 4A is a gel showing expression of a synthetic *P. putida* methionine gamma lyase synmdeA in BL21/pTM vector prior to and after induction with IPTG. All cutures were grown at 37° C. synmdeA was cloned into pED15b under the control of T7 RNA polymerase promoter. Lanes are: M—prestained protein molecular weight standards, high range, as indicated on the figure; 1 and 2—three hours induction with 0.1 mM IPTG; 3—three hours induction with 0.5 mM IPTG; 4—three hours induction with 1 mM IPTG; 5—three hours induction with 2 mM IPTG; 6—not induced.

FIG. 4B is a gel showing the poor expression of native *P. putida* methionine gamma lyase (mdeA) in pSIT vector prior to and after induction with IPTG. All cutures were grown at 37° C. The induced samples contain extra bands at about 28 kD due to premature termination of mdeA translation. Native mdeA was cloned into the pSIT vector under the control of the T7 RNA polymerase promoter. Lanes are: M—prestained protein molecular weight standards, high range, as indicated on the figure; 1—not induced; 2 and 3—three hours induction with 0.5 mM IPTG; 4 and 5—three hours induction with 1 mM IPTG.

FIG. 5 shows expression in *E. coli* of two genes with very different $\Delta G_{folding}$, naphthalene dioxygenase (NDO) from *Pseudomonas putida* ($\Delta G$=−256.1 kcal/mol) and methionine gamma lyase (mgl I) from *T vaginalis* ($\Delta G$=−152.5 kcal/mol). Lanes 1–4 are NDO products, and 5–9 are MGL 1 products. Lanes are as follows: M1—multimark multicolored standard; M2—prestained protein molecular weight standards; 1—not induced; 2—three hours induction with 0.02% L-arabinose; 3—three hours induction with 0.04% L-arabinose; 4—three hours induction with 0.08% L-arabinose; 5—not induced; 6—three hours induction with 0.02% L-arabinose; 7—three hours induction with 0.04% L-arabinose; 8—three hours induction with 0.08% L-arabinose; 9—three hours induction with 0.10% L-arabinose. Both genes were cloned into the pBAD vector. Cells were grown at 37° C. Expression of mglI, having a less negative $\Delta G_{folding}$ was superior to NDO expression.

DETAILED DESCRIPTION OF THE INVENTION

Figure 3:
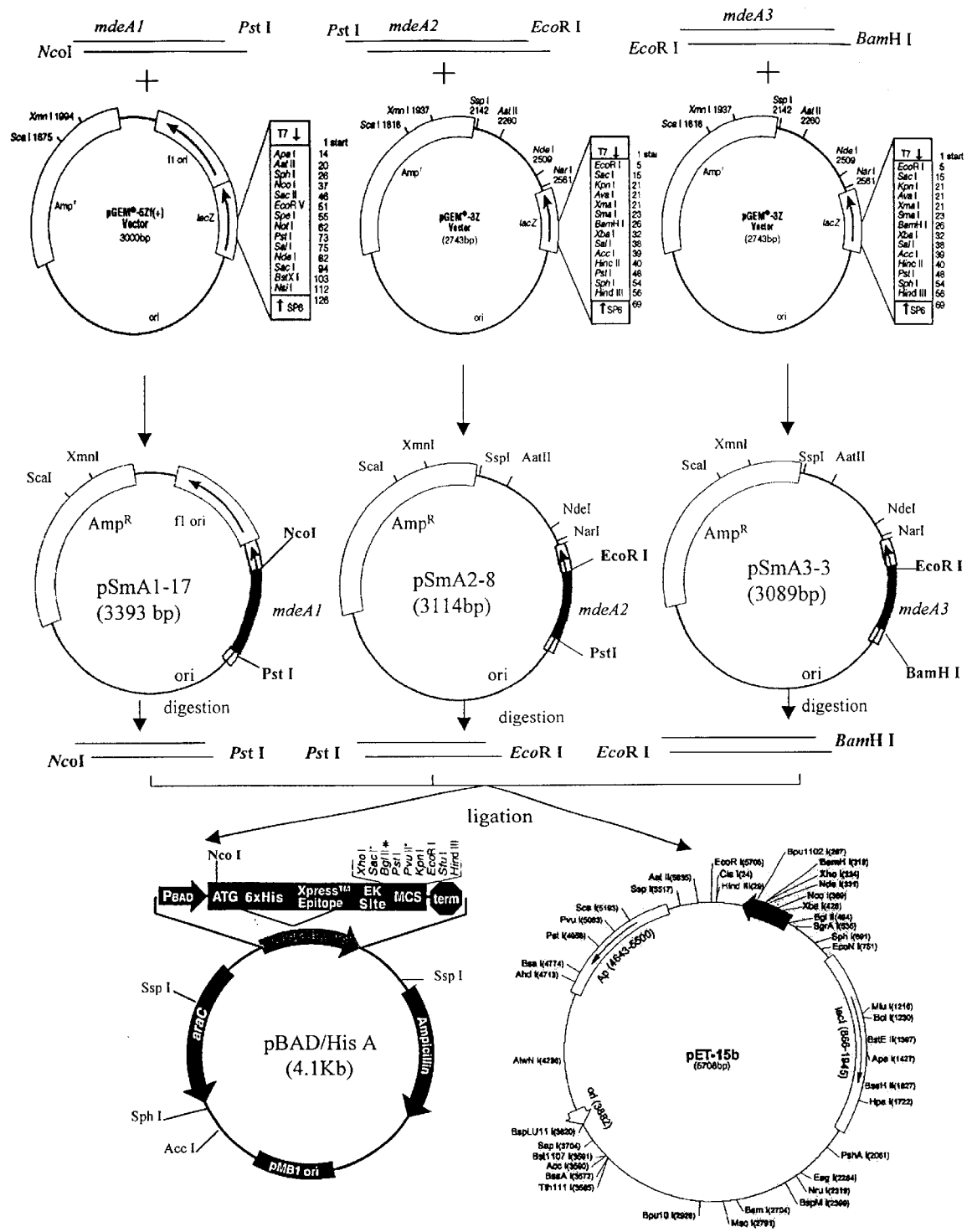
FIG. 3 is a schematic of the cloning strategy for mdeA1, mdeA2 and mdeA3 into cloning and expression vectors. The amplified segments are ligated into the multiple cloning site of the illustrated vector in the top row, then *E. coli* are transformed with the plasmids. Individual plasmids containing each segment are selected in the second row, and the plasmids are double-digested to extract the insert, which is then ligated into an expression vector as shown in the last row.

In one embodiment, the invention is directed to developing nucleic acid sequences that enhance expression of the encoded protein in a heterologous host. The frequency of particular codon usage for *E. coli* and other enteric bacteria is shown in Table 1, below. This table is derived from the 2000 Novagen Catalog, page 196, available online at http://www.novagen.com/html/catfram.html; herein incorporated by reference. However, the information in this table does not tell one of skill in molecular biology which codons should be replaced to enhance expression, if indeed any replacements will enhance expression. Considerations other than simple codon replacement are clearly important. It has been discovered that the composition of the full gene (or fragment to be expressed) is more important than a particular codon exchange, and heterologous expression can be enhanced by replacement of codons in the sequence's open reading frame alone, independent of promotors or other regulatory sequence.

TABLE 1

| aa | Codon | /1000[1] | Fraction[2] |
| --- | --- | --- | --- |
| Gly | GGG | 1.89 | 0.02 |
| Gly | GGA | 0.44 | 0.00 |
| Gly | GGU | 52.99 | 0.59 |
| Gly | GGC | 34.55 | 0.38 |
| Glu | GAG | 15.68 | 0.22 |
| Glu | GAA | 57.20 | 0.78 |
| Asp | GAU | 21.63 | 0.33 |
| Asp | GAC | 43.26 | 0.67 |
| Val | GUG | 13.50 | 0.16 |
| Val | GUA | 21.20 | 0.26 |
| Val | GUU | 43.26 | 0.51 |
| Val | GUC | 5.52 | 0.07 |
| Ala | GCG | 23.37 | 0.26 |
| Ala | GCA | 25.12 | 0.28 |
| Ala | GCU | 30.78 | 0.35 |
| Ala | GCC | 9.00 | 0.10 |
| Arg | AGG | 0.15 | 0.00 |
| Arg | AGA | 0.00 | 0.00 |
| Ser | AGU | 1.31 | 0.03 |
| Ser | AGC | 10.31 | 0.20 |
| Lys | AAG | 16.11 | 0.26 |
| Lys | AAA | 46.46 | 0.74 |
| Asn | AAU | 2.76 | 0.06 |
| Asn | AAC | 39.78 | 0.94 |
| Met | AUG | 24.68 | 1.00 |
| Ile | AUA | 0.15 | 0.00 |
| Ile | AUU | 10.16 | 0.17 |
| Ile | AUC | 50.09 | 0.83 |
| Thr | ACG | 3.63 | 0.07 |
| Thr | ACA | 2.03 | 0.04 |
| Thr | ACU | 18.87 | 0.35 |
| Thr | ACC | 29.91 | 0.55 |
| Trp | UGG | 7.98 | 1.00 |
| stop | UGA | 0.00 | (stop) |
| Cys | UGU | 3.19 | 0.49 |
| Cys | UGC | 3.34 | 0.51 |
| stop | UAG | 0.00 | (stop) |
| stop | UAA | 0.00 | (stop) |
| Tyr | UAU | 7.40 | 0.25 |
| Tyr | UAC | 22.79 | 0.75 |

TABLE 1-continued

| aa  | Codon | /1000[1] | Fraction[2] |
|-----|-------|----------|-------------|
| Leu | UUG   | 2.61     | 0.03        |
| Leu | UUA   | 1.74     | 0.02        |
| Phe | UUU   | 7.40     | 0.24        |
| Phe | UUC   | 24.10    | 0.76        |
| Ser | UCG   | 2.03     | 0.04        |
| Ser | UCA   | 1.02     | 0.02        |
| Ser | UCU   | 17.42    | 0.34        |
| Ser | UCC   | 19.02    | 0.37        |
| Arg | CGG   | 0.15     | 0.00        |
| Arg | CGA   | 0.29     | 0.01        |
| Arg | CGU   | 42.10    | 0.74        |
| Arg | CGC   | 13.94    | 0.25        |
| Gln | CAG   | 33.83    | 0.86        |
| Gln | CAA   | 5.37     | 0.14        |
| His | CAU   | 2.61     | 0.17        |
| His | CAC   | 12.34    | 0.83        |
| Leu | CUG   | 69.69    | 0.83        |
| Leu | CUA   | 0.29     | 0.00        |
| Leu | CUU   | 3.63     | 0.04        |
| Leu | CUC   | 5.52     | 0.07        |
| Pro | CCG   | 27.58    | 0.77        |
| Pro | CCA   | 5.23     | 0.15        |
| Pro | CCU   | 2.76     | 0.08        |
| Pro | CCC   | 0.15     | 0.00        |

[1]Expected number of occurrences per 1000 codons in enteric bacterial genes whose codon usage is identical to that compiled in the frequency table.
[2]Fraction of occurrences of the codon in its synonymous codon family.

The present invention encompasses highly amplifiable, expressible genes and is directed to methods of designing and physically creating these genes. In one embodiment, the present invention is directed to a method of designing and physically creating genes that express well when introduced into enteric bacterial host microorganisms such as $E.\ coli$. The invention allows expression of genes from various bacteria, including streptomycetes, Bacillus, Pseudomonas and the like in hosts such as $E.\ coli$ at commercially viable levels, even proteins with typically low yields, such as methionine gamma-lyase from $P.\ putida$. As used herein, the terms "polypeptide," "protein" and "amino acid sequence" are used interchangeably and mean oligomeric polyamides of at least two amino acids, whether or not they encompass the full-length polypeptide encoded by a gene or merely a portion of it. "Heterologous" indicates that the sequence is not native to the host used or identical to a sequence which naturally occurs in the host used, or refers to a host which is not the natural source of a nucleic acid or peptide sequence. "Designing" means conceiving a sequence of nucleotides in a form that can be written or printed. Such sequence may correspond to the coding region of an entire gene, or only a portion of it, and may also include additional bases added at a particular location or position, for example to create desired restriction sites. "Physically creating" means preparing a chemical entity such as an oligonucleotide or polypeptide, whether by synthesis by chemical and/or enzymatic methods, biosynthesis, a combination of synthesis and PCR, or by any other methods known in the art. "PCR" means polymerase chain reaction.

In the present invention, the sequence of a gene is modified to enhance its ability to be amplified, for example by PCR methods, and/or to improve its expression in a selected host, for example, an enteric bacterium such as $E.\ coli$. This is achieved by designing a nucleotide sequence, using codons preferred by the host, calculating the $\Delta G_{folding}$ of the nucleic acid sequence (the amount of energy required for or released by folding in solution in kcal/mole), modifying the sequence by replacing one or more codons in the sequence in one or more areas of predicted secondary structure with less preferred codons to reduce predicted secondary structure, and recalculating the $\Delta G_{folding}$ of the modified nucleic acid sequence. The replacement of codons and recalculation of the free energy of folding may be repeated as many times as desired. The result is a modified final nucleic acid sequence, for example a synthetic gene encoding a desired complete or partial protein, whether a mutant protein or one having the desired structural and functional attributes of a native protein.

As used herein, the term "synthetic" gene, nucleic acid, oligonucleotide, or primer or the like means a nucleic acid sequence that is not found in nature; in other words, not merely a heterologous sequence to a particular organism, but one which is heterologous in the sense that it has been created in a laboratory and is altered in some way, and does not have exactly the sequence that its naturally occurring source or template has. This can include, for example, nucleic acid sequences derived from wholly artificial amino acid sequences, or nucleic acid sequences with single or multiple nucleotide changes as compared to the naturally occurring sequence, those created by random or directed mutagenesis, chemical synthesis, or by any means known to one of skill in the art (see e.g., techniques described in Sambrook et al., "Molecular Cloning; A Laboratory Manual," Cold Spring Harbor Laboratory Press (1989), herein incorporated by reference). Such alterations can be done without changing the amino acid sequence encoded by the nucleic acid sequence, or can modify the amino acid sequence to leave a desired function of the encoded protein unaltered or enhanced. As used herein, "nucleic acid" means a naturally occurring or synthetic nucleic acid, which can be composed of natural or synthetic nitrogen bases, a deoxyribose or ribose sugar, and a phosphate group.

"Secondary structure" refers to regions of a nucleic acid sequence that, when single stranded, have a tendency to form double-stranded hairpin structures or loops. Such structures impede transcription (or amplification in vitro) and translation of affected regions in the nucleic acid sequence. Nucleic acids can be evaluated for their likely secondary structure by calculating the predicted $\Delta G_{folding}$ of each possible structure that could be formed in a particular strand of nucleic acid. Energy must be released overall to form a base-paired structure, and a structure's stability is determined by the amount of energy it releases. The more negative the $\Delta G_{folding}$ (i.e., the lower the free energy), the more stable that structure is and the more likely the formation of that double-stranded structure.

Computer programs exist that can predict the secondary structure of a nucleic acid by calculating its free energy of folding. One example is the mfold program, which can be found at http://mfold2.wustl.edu/~mfold/dna/form1.cgi (using free energies derived from SantaLucia Proc. Natl. Acad. Sci. USA 95:1460–1465 (1998); see also Zuker, Science, 244, 48–52, (1989); Jaeger et al., Proc. Natl. Acad. Sci. USA, Biochemistry, 86:7706–7710 (1989); Jaeger et al., Predicting Optimal and Suboptimal Secondary Structure for RNA. in "Molecular Evolution: Computer Analysis of Protein and Nucleic Acid Sequences", R. F. Doolittle ed., Methods in Enzymology, 183,281–306 (1989); all herein incorporated by reference). Another example of such a computer program is the Vienna RNA Package, available at http://www.ks.uiuc.edu/~ivo/RNA/, which predicts secondary structure by using two kinds of dynamic programming algorithms: the minimum free energy algorithm of Zuker and Stiegler (Nuci. Acid. Res. 9: 133–148 (1981)) and the partition function algorithm of McCaskill (Biopolymers 29, 1105–1119 (1990)). Distances (dissimilarities) between secondary structures can be computed using either string alignment or tree-editing (Shapiro & Zhang 1990). Finally, an algorithm is provided to design sequences with a predefined structure (inverse folding).

Modifications to reduce secondary structure in DNA sequences by altering codon usage can be made in several ways. As used herein, "replacing codons" or "altering codon usage" means altering at least one of the nucleotides making up the three nucleotides of the codon triplet. It is understood that this change can occur at a "wobble" position to leave the amino acid encoded unchanged, or at another position or to a base that results in a change in the encoded amino acid. For example, the codon changes can be designed to swap out codons for a particular amino acid in the sequence (e.g., at a designated position in the sequence) which are not common in the selected host (following e.g., Kane, supra, or Zahn, supra). Further, codons can be replaced to reduce the G-C content of the naturally occurring codon.

The inventive methods of the present invention produce sequences with superior expression characteristics because it takes more than one variable into account. The methods involve designing a nucleic acid sequence based on a desired amino acid sequence using the codons most commonly used for each amino acid in the chosen host organism. Next, the predicted free energy of folding for the designed sequence is calculated using a computer program as described previously. The program mfold is used in the Examples provided herein, although any similar program may be used in the practice of this invention. In calculating the predicted $\Delta G_{folding}$, the full-length nucleotide sequence can be analyzed as a single entity, or the full-length sequence can be divided into shorter segments and the predicted $\Delta G_{folding}$ for each segment can be calculated separately, and then added together. After the predicted $\Delta G_{folding}$ is calculated, changes to the sequence are made to try to reduce the formation of secondary structure. Regions of predicted secondary structure are identified using, for example, one of the computer programs previously described, and changes are made in codons in these identified regions. Thus, one or more codons in regions of predicted high secondary structure are changed to the second or third most commonly used codon choice for the chosen host organism, and the predicted $\Delta G_{folding}$ is recalculated. This process of codon changes and recalculation of the predicted $\Delta G_{folding}$ is repeated until the predicted $\Delta G_{folding}$ of the sequence examined (e.g., the entire sequence or a portion) is increased (made less negative) by greater than about 2%, preferably greater than about 10%, more preferably greater than about 30%, as calculated by $\Delta G_{folding}$/(number of bases in the sequence analyzed). The starting sequence for the step of designing a sequence (e.g., the naturally occurring sequence) is set as 100%. It is likely that the change in $\Delta G_{folding}$ between the starting sequence and the final product will be smaller when the starting sequence is a completely synthetic sequence based solely on preferred codon usage than when the starting sequence is a naturally occurring sequence from a heterologous organism. $\Delta G_{folding}$ for segments analyzed separately can be added to arrive at a $\Delta G_{folding}$ for the entire sequence, or the $\Delta G_{folding}$ for the entire sequence can be determined in a single calculation. Once the $\Delta G_{folding}$ for the entire sequence has been so determined, it is divided by the sequence length in bases to arrive at a uniform measure of $\Delta G_{folding}$ for comparison of sequences of unequal length.

Several variants can be analyzed to illustrate the advantages of the inventive method, summarized in Table 2 below. A naturally occurring mdeA gene from *P. putida* (SEQ. ID NO. 1) was used as the starting sequence, and its $\Delta G_{folding}$ was calculated (all $\Delta G_{folding}$ results reported herein were carried out assuming a temperature of 37° C., Na+=1 M, and Mg++=0) and set at 100%. This sequence was modified by replacing rare arginine codons (termed "repmdeA;" modifications derived from Zahn, supra) with one found most commonly in *E. coli* (SEQ ID NO. 28). The change in $\Delta G_{folding}$/base from this replacement was 1.9%. A more significant alteration of mdeA was performed by replacing all of the rare codons mentioned in Kane, supra. This sequence was made by exchanging agg, aga, and cga codons with cgt (arginine), cta codons with ctg (leucine), ata with atc (isoleucine), and ccc with ccg (proline) (termed "raremdeA;" SEQ ID NO. 29). As seen in Table 2, below, this exchange also did not significantly impact the $\Delta G$ of the sequence, resulting in a change in $\Delta G_{folding}$/base of only 1% as compared to the native sequence. Simply replacing a rare codon does not necessarily increase $\Delta G_{folding}$, and in fact, could lower $\Delta G_{folding}$, creating or failing to resolve problems in transcription or translation, or in amplification by PCR methods.

Because the codons known in the art to be rare and potentially to have an impact on expression did not significantly improve the $\Delta G_{folding}$ of the sequence, all codons of mdeA's open reading frame were exchanged for the most common codons in enteric bacteria from Table 1, above (a sequence termed "optmdeA," SEQ ID NO. 30). The $\Delta G_{folding}$ of this sequence was increased 31.8% by this change compared to mdeA, a significant improvement. However, when the sequence optmde A was analyzed for regions of predicted secondary structure, replacements of codons in areas of high secondary structure were made to generate the designed sequence synmdeA (SEQ ID NO. 3). The predicated $\Delta G_{folding}$ was recalculated for this sequence, and a superior sequence with a greatly improved $\Delta G_{folding}$ was created. In this case, $\Delta G_{folding}$ was increased (made less negative) by 40.7% compared to the starting native sequence. Thus, it is clear that the inventive methods of developing the synthetic sequences go well beyond any suggestions in the art pertaining to codon exchange.

TABLE 2

| Sequence | $\Delta G$ (kcal/mol) | $\Delta G$/base | % Change in $\Delta G$ |
|---|---|---|---|
| mdeA (1197 bp) | −256.6 | −0.214 | 0% |
| repmdeA (1197 bp) | −251.8 | −0.210 | 1.9% |
| raremdeA (1197 bp) | −254.0 | −0.212 | 1.0% |
| optmdeA (1200 bp) | −175.5 | −0.146 | 31.8% |
| synmdeA (1200 bp) | −152.5 | −0.127 | 40.7% |

The method described herein of formulating synthetic sequences for improved expression can be used for any nucleic acid sequence, even those being expressed in homologous hosts, or with relatively little predicted secondary structure. Most commonly, however, the need to improve expression will arise when expressing proteins in heterologous hosts. Regardless, any starting sequence, preferably with a $\Delta G_{folding}$/base of about −0.05 kcal/(mole)(base) or less, and more preferably with a $\Delta G_{folding}$/base of about −0.15 kcal/(mole)(base) or less, and most preferably with a $\Delta G_{folding}$/base of −0.2 kcal/(mole)(base) or less can be improved for better expression using the methods of the invention. When a $\Delta G_{folding}$ less than about −0.20 kcal/(mole)(base) or an increase of at least about 2% from the starting sequence is reached, the actual sequence of the synthetic DNA can be physically created. Such physical creation of the designed oligonucleotide sequence can be accomplished by any of the methods known in the prior art, for example by oligonucleotide synthesis.

Additionally, the invention takes advantage of the improved secondary structure characteristics of the synthetic nucleic acid for enhanced amplification capability, for example using PCR methods. Some of the same features of native nucleic acid sequence that make them difficult to express in heterologous hosts may also make them difficult to clone or amplify. High secondary structure in one or more regions of the nucleic acid can make cloning or PCR difficult or impossible to perform on the intact nucleic acid or even on segments of the nucleic acid. However, using the methods of the invention to reduce the secondary structure, the resulting nucleic acid templates have better properties for polymerization and amplification. Making synthetic nucleic acids that amplify easily has important ramifications for common molecular biology procedures such as site directed mutagenesis. For example, using the methods of the invention, a nucleic acid sequence encoding a particular protein (a native protein or a protein with one or more desired mutations) can be designed using codons used more commonly in a desired expression host cell, and the predicted $\Delta G_{folding}$ may then optimized as described herein. Regardless of the features of the polymerase, or any particular weaknesses it may have (e.g., poor processivity), the probability of accurate full length synthesis of the copy strand from the template is improved using the synthetic nucleic acid of the invention because the regions of secondary structure have been reduced. Codons are replaced overall to minimize $\Delta G_{folding}$, in kcal/(mole)(base), but in specific locations also to alter the amino acid sequence encoded by the nucleotide sequence, resulting in a nucleic acid sequence encoding a particular protein with improved amplification and expression properties.

In one embodiment of this invention, the design and preparation of synthetic genes are used in application of directed evolution, gene shuffling and molecular breeding methods. Examples of gene shuffling and molecular breeding are described in U.S. Pat. Nos. 5,605,793, 5,811,238, 5,830,721, 5,837,458, 5,965,408, 5,958,672, 6,001,574, all herein incorporated by reference. Genes to be shuffled or recombined are designed and/or physically created based on the incorporation of preferred codons as described in the present invention. The advantage of the use of genes designed and physically created as described herein is the improved expression of the shuffled or recombined genes. Such improved expression facilitates screening by providing higher levels of the gene products that are to be detected. The time required for screening can be reduced, or certain enzymatic activities can be detected more easily. Improvements in gene products, whether enzymes or metabolites produced by the actions of two or more different proteins derived through molecular breeding or directed evolution methods, can be detected more readily. Genes designed and produced according to the methods of the present invention can also be incorporated into kits for screening or other purposes. An example of an enzyme screening kit is found in U.S. Pat. No. 6,004,788, herein incorporated by reference.

Another embodiment of the invention, illustrated in the examples below, involves an improved method of synthesizing a nucleic acid. Usual methods of synthesizing a desired nucleic acid sequence which is not found in nature involves difficult and expensive chemical synthesis. The synthesis method of the invention to create a synthetic sequence involves an amplification method, such as PCR, using synthesized oligonucleotides designed to be overlapping, having as many adjacent sense and antisense strands as desired or required to complete the synthetic gene of choice. The oligonucleotides serve as both the template and primer in this PCR-based synthesis strategy.

The examples described herein demonstrate one implementation of the method for the physical creation of a synthetic gene. Two rounds of PCR reactions were carried out on three segments of the synmdeA gene, and six oligonucleotides per segment were used to construct the synthetic gene. The segments were ligated, amplified, excised, and inserted into an expression vector. The first round of amplification involved creating four long oligonucleotides (around 100 bps) based on the synthetic sequence. These long oligonucleotides were used to generate template DNA for various segments of the sequence. Longer synthetic sequences are best broken into shorter segments in this method for easier amplification. The first round PCR amplification relies on overlapping sections of each long oligonucleotide, to create areas of overlap. The areas of overlap serve to prime the extension of the neighboring segment. The areas of overlap can be any length that is sufficient for specificity and long enough for polymerase recognition/attachment, preferably at least 10 bases and more preferably at least 15 bases of overlap.

The second round of amplification used two short oligonucleotides (each about 30 nucleotides) to amplify the full-length segments. The short oligonucleotides overlap the 5' ends of the sense and antisense strands from the previous round to form a template of each segment primed by the first round strands, resulting in the filling in of both 5' and 3' ends after the second round of PCR. The segments derived from this two-round PCR are ligated together to form the unitary synthetic sequence. Preferably, this is facilitated using naturally occurring or synthesized restriction sites. Such sites enhance unidirectional cloning, ligation, etc.

It is understood that any nucleic acid and any reaction conditions that do not require exactly this sort of overlap and/or priming (e.g., RNA, RNA polymerases) can be used to create a modified nucleic acid of the invention without departing from the scope of the invention, and that other means of synthesizing the desired gene of interest are possible using methods known in the art. It is further understood that the gene or nucleic acid can be synthesized in one or several pieces. Likewise, many vectors and host species and strains other than those used herein can be used successfully in the practice of the invention.

The invention is described more fully in the following Examples, which are presented for illustrative purposes only and are not intended to limit the scope of the invention. In the embodiment of the invention disclosed by the Examples, a synthetic gene was designed which encodes the enzyme methionine gamma-lyase. Methods and vectors for its cloning and expression are provided, although other methods/vectors can be used.

EXAMPLE 1

Design of a Synthetic Gene Sequence

In these Examples, a specific synthetic gene sequence is disclosed encoding naturally occurring *P. putida* methionine gamma-lyase gene sequence, and consists of codons common to enteric bacteria such as *E. coli*. Also described are three gene fragments derived from the complete synthetic methionine gamma-lyase gene that have unique cloning sites at each end of each fragment.

Materials

DNA taq polymerase and T4 DNA ligase were purchased from Roche (Branchburg, N.J.). Restriction endonucleases were purchased from New England Biolabs. pET 15b expression vector and *E. coli* BL21(DE3) were obtained from Donnald Nierlich (UCLA, California). pBAD expression vector and *E. coli* LMG 194 were purchased from Invitrogen (Carlsbad, Calif.). pGEM-3Z, pGEM-5Zf(+) cloning vectors and *E. coli* JM109 were purchased from Promega (Madison, Wis.). The oligonucleotides for PCR amplification were synthesized by IDT Inc. (Coralville, Iowa). QIAquick gel extraction kit and QIAprep spin miniprep kit were purchased from QIAGEN, Inc. (Valencia, Calif.).

Equipment

Thermocycler Perkin Elmer model 9600 (1991).

Centrifuge

Water bath incubator

Culture incubator

Electrophoresis devices

Software mfold—Prediction of RNA secondary structure by free energy minimization; Versions 2.0 and 3.0: suboptimal folding with temperature dependence. Michael Zuker and John Jaeger; Macintosh version developed by Don Gilbert DNA strider 1.01—a C program for DNA and protein sequence analysis designed and written by Christian Marck. Service de Biochime-Departement de Biologie, Institut de Recherche Fondamentale Commissariat a l'Energie Atomique- France HyperPCR—a Hypercard v.20 stack to determine the optimal annealing temperature for PCR reaction and complementarity between the 3' ends of the two oligos and for internal complementarity of each 3' end. Developed by Brian Osborne, Plant Gene Expression Center, 800 Buchanan St., Albany, Calif. 94710

Amplify 1.2—for analyzing PCR experiments. Bill Engels 1992, University of Wisconsin, Genetics, Madison, Wis. 53706, WREngels@macc.wisc.edu Design of Synthetic DNA Sequence Encoding *Pseudomonas putida* Methionine Gamma-lyase.

The DNA sequence of naturally occurring mdeA gene was obtained from Entrez nucleotide Query (NID g2217943) (SEQ ID. NO. 1). Based on this DNA sequence and the amino acid sequence deduced from its open reading frame, several of the original codons were changed to codons that are more commonly used in enteric bacteria. The resulting designed sequence is shown in FIG. IA (SEQ ID NO. 2). After changing codons to those more commonly used in *E. coli*, the computer program mfold was run to calculate the predicted $\Delta G_{folding}$ the sequence. The computer program was then used to generate an image of the predicted oligonucleotide, and regions of predicted secondary structure were identified. Codons in regions of high secondary structure were changed to the second most commonly used codon for that amino acid in *E. coli*, and the predicted $\Delta G_{folding}$ the sequence was recalculated.

In addition, the sequence was modified to incorporate a non-naturally occurring glycine at amino acid position 2. The synthetic sequence therefore does not encode a protein identical to the naturally occurring polypeptide encoded by the *P. putida* methionine gamma-lyase gene. The modification of the sequence was incorporated to facilitate unidirectional cloning of the synthetic sequence into the cloning and expression vectors using an Nco I restriction site. The modified DNA sequence was termed synmdeA (SEQ ID NO.2). In this Example, approximately fifty percent of the codons were changed from those found in the naturally-occurring gene.

EXAMPLE 2

Amplification of the Synthetic DNA Fragments mdeA1, mdeA2, mdeA3

Oligonucleotide Design

Oligonucleotide primers were synthesized on the basis of the nucleic sequence of the synmdeA gene, whose sequence was determined from the process described in Example 1. The synmdeA gene, with 1200 bps of coding sequence (1207 bps with residual bases from restriction sites included) (SEQ ID NO. 3), was broken down into three fragments, mdeA1, mdeA2, and mdeA3. The first cloning fragment, mdeA1, contained a Nco I cloning site at the 5' end and a Pst I cloning site at the 3' end, and was 426 bps after the double stranded product was digested (SEQ ID NO.4), 441 bps after second round amplification but before digestion (FIG. 1B; SEQ ID NO. 5). The second cloning fragment, mdeA2, contained a Pst I cloning site at the 5' end and an EcoRI cloning site at the 3' end, and was 410 bps after digestion (SEQ ID NO. 6), 430 bps after second round amplification but before digestion (FIG. 1C; SEQ ID NO. 7). The third one, mdeA3, contained an EcoR I cloning site at the 5' end and a BamH I cloning site at the 3' end, and was 366 bps after digestion (SEQ ID NO. 8), 383 bps after second round amplification but before digestion (FIG. 1D; SEQ ID NO. 9). The segments were the product of internal restriction sites occurring in the synmdeA sequence. Restriction sites were chosen that roughly divided the sequence into three equal segments, and which correspond to common multiple cloning sites on commercially available vectors.

To synthesize the segments, or fragments, four long oligonucleotides (98–117 bps), and two short oligonucleotides (~30 bps) were designed for each fragment, and with the help of computer software, their self-folding secondary structures were minimized as much as possible in order to maximize the DNA synthesis during PCR reactions. All the oligonucleotides had secondary structure $\Delta G$'s less negative than the $\Delta G$'s of the two overlapping annealed fragments, decreasing the probability of secondary structure forming instead of oligonucleotide hybridization.

Two short oligonucleotides and four long oligonucleotides were designed for each of the three segments. They were designed to have 17 to 18 bps overlap with each other. Underlined nucleotides indicate the annealing regions between two adjacent oligonucleotides.

1. First Segment of synmdeA: mdeA1

The sequences of these oligonucleotides was as follows:

mdePr1-1(33 bps): 5' CAA GAG GCC ATG GGT <u>CAC GGC TCC AAC AAA CTG</u> 3' (sense) (SEQ ID NO. 10)

mdePr1-2 (114 bps): 5' <u>CAC GGC TCC AAC AAA CTG</u> CCG GGC TTT GCT ACC CGC GCT ATC CAC CAC GGT TAT GAC CCG CAG GAT CAC GGT GGT GCA CTG GTT CCG CCG GTT TAC <u>CAG ACT GCT ACT TTC ACC 3</u>'(sense) (SEQ ID NO. 11)

mdePr1-3 (116 bps): 5' <u>GC TTC CAG CAG GTT CAG</u> GGT CGG GTT GGA GAT ACG GGA GTA GAA GTG ACC AGC CTG TTC GCC AGC AAA GCA CGC AGC GCC GTA TTC AAC GGT CGG GAA <u>GGT GAA AGT AGC AGT CTG 3'</u> (antisense) (SEQ ID NO. 12)

mdePr1-4 (117 bps): 5' <u>CTG AAC CTG CTG GAA GCA</u> CGT ATG GCA TCT CTG GAA GGC GGC GAA GCT GGT CTG GCG CTG GCA TCT GGT ATG GGC GCG ATC ACC TCT ACC CTG TGG ACC <u>CTG CTG CGT CCG GGT GAC</u> 3' (sense) (SEQ ID NO. 13)

mdePr1-5 (116 bps): 5' <u>GC CAT ATC TAC GTG ACG</u> CAG TTT AAC GCC GAA TTC ACC GAT ACC GTG GTG CAG GAA AGC AAA AGT ACA ACC ATA CAG GGT GTT GCC CAG CAG AAC TTC <u>GTC ACC CGG ACG CAG CAG</u> 3'(antisense) (SEQ ID NO. 14)

mdePr1-6 (33 bps): 5' CAG TGC CTG CAG GTC <u>AGC CAT ATC TAC GTG ACG</u> 3' (antisense) (SEQ ID NO. 15)ps 2. Second Segment, mdeA2

The sequences of these oligonucleotides was as follows:

mdePr2-1 (33 bps): 5' GCT GAC CTG CAG GCA <u>CTG GAA GCG GCT ATG ACC</u> 3' (sense) (SEQ ID NO. 16)

mdePr2-2 (114 bps): 5' <u>CTG GAG GCT GCT ATG ACC</u> CCG GCT ACC CGT GTT ATC TAC TTC GAA TCC CCG GCT AAC CCG AAC ATG CAC ATG GCT GAC ATC GCA GGT GTT GCT AAA <u>ATC GCT CGT AAG CAC GGC</u> 3' (sense) (SEQ ID NO. 17)

mdePr 2-3(115 bps): 5' <u>G GTA TTT AGT AGC GGA GTG</u> AAC AAC CAG GTC AGC GCC CAG TTC CAG CGG ACG TTG CAG GTA CGG AGT ACA GTA GGT GTT ATC AAC AAC TAC GGT AGC <u>GCC GTG CTT ACG AGC GAT</u> 3' (antisense) (SEQ ID NO.18)

mdePr2-4 (111 bps): 5' <u>CAC TCC GCT ACT AAA TAC CTG TCC GGC CAC</u> GGC GAC ATC ACT GCT GGC ATC GTA GTA GGC TCC CAG GCA CTG GTT GAC CGT ATC CGT CTG CAA <u>GGT CTG AAA GAC ATG ACC</u> 3' (sense) (SEQ ID NO. 19)

mdePr2-5 (115): 5' <u>G TAC CTG AGC GTT AGC ACA</u> GTG ACG GTC CAT ACG CAG GTT CAG GGT CTT GAT ACC ACG CAT CAG CAG TGC TGC GTC GTG CGG GGA CAG AAC AGC GCC <u>GGT CAT GTC TTT CAG ACC</u> 3' (antisense) (SEQ ID NO. 20)

mdePr2-6 (33): 5' C CAG GAA TTC AGC CA <u>G TAC CTG AGC GTT AGC AC</u> 3'(antisense) (SEQ ID NO. 21)

3. Third Segment, mdeA3

The sequences of these oligonucleotides was as follows:

mdePr3-1 (31 bps): 5' T CTT AAT <u>GAA TTC CTG GCT CGT CAG CCG CAG</u> 3' (sense) (SEQ ID NO. 22)

mdePr3-2 (105 bps): 5' <u>CTG GCT CGT CAG CCG CAG</u> GTA GAA CTG ATC CAC TAT CCG GGC CTG GCT TCC TTC CCG CAG TAC ACT CTG GCA CGT CAG CAG ATG TCC <u>CAG CCG GGC GGT ATG ATC</u> 3' (sense) (SEQ ID NO. 23)

mdePr3-3 (106 bps): 5' <u>C GTC ACC CAG GGA AAC CGC</u> ACG GGA GAA CAG CTG CAG AGC GTT CAT GAA ACG ACG ACC AGC GCC GAT GCC ACC CTT CAG TTC GAA AGC <u>GAT CAT GCC ACC CGG CTG</u> 3' (antisense) (SEQ ID NO. 24)

mdePr3-4 (106 bps) 5' <u>GCG GTT TCC CTG GGT GAC</u> GCT GAA TCC CTG GCG CAG CAC CCG GCA TCC ATG ACT CAC TCC TCC TAC ACT CCG GAA GAA CGT GCG CAC <u>TAC GGC ATC TCC GAA GGC C</u> 3' (sense) (SEQ ID NO. 25)

mdePr3-5 (98 bps): 5' <u>CA AGC GCT AGC CTT CAG AGC</u> CTG CTG AAC GTC TGC CAG CAG ATC ATC GAT GTC TTC CAG ACC AAC AGA CAG ACG AAC CA <u>G GCCTTC GGA GAT GCC GTA</u> 3' (antisense) (SEQ ID NO. 26)

mdePr3-6 (32 bps): 5' T GGT GGA TCC T <u>CA AGC GCT AGC CTT CAG AGC C</u> 3' (antisense) (SEQ ID NO. 27)

Amplification of Segmental DNA: mdeA1, mdeA2, mdeA3

Each segment synthesis took two rounds of amplification. The first round was to generate the template for the second round using the four long oligonucleotides with overlapping ends (e.g., 3' or 5' sense ends overlapping neighboring 5' or 3' antisense ends). The second round amplification was using the two short nucleotides and the template from the first. Standard PCR reaction mixture was used with 100 µl reaction volume, 0.2 mM dNTPs (final concentration), and 60 to 90 pmoles of each oligonucleotide.

To synthesize the template for mdeA1, termed tpA1, mdePr1-2 (71 pmoles), mdePr 1-3 (74 pmoles), mdePr1-4 (77 pmoles), and mdePr1-5 (64 pmoles) were used. MdePr2-2 (64 pmoles), mdePr2-3 (73 pmoles), mdePr2-4 (67 pmoles), and mdePr2-5 (74 pmoles) were used to synthesize mdeA2 template, termed tpA2. To synthesize mdeA3 template, termed tpA3, mdePr3-2 (66 pmoles), mdePr3-3 (626 pmoles), mdePr3-4 (60 pmoles), and mdePr3-5 (82 pmoles) were used. The strategy is shown in FIG. 2A. Based on the estimated annealing temperatures between the oligonucleotides above, the PCR reaction conditions were as follows: first denaturation at 94° C. for 2 min; then 10 cycles of denaturation at 94° C. for 30 sec; annealing at 51° C. for 40 sec, and extension at 72° C. for 1 min. This was followed by 20 cycles of denaturation at 94° C. for 30 sec; 65° C. for 55 sec; 72° C. for 1 min; then a final extension at 72° C. for 7 min. The PCR was carried out using a Perkin-Elmer Gene Amp 9600.

The PCR products were separated on 2% agarose gels run with a 1 kb DNA ladder (NEB); product bands of the expected size (411 bps for tpA1, 401 bps for tpA2, and 360 bps for tpA3) were cut out and extracted using QIAquick gel extraction kit. The products were then used as the templates for second round PCR reactions to synthesize mdeA1, mdeA2, and mdeA3 DNAs. The strategy for the second round amplification is shown in FIG. 2B.

For the second round, mdePr1-1(80 pmoles), mdePr1-6 (67 pmoles), and 1 µl of 50 µl gel purified template tpA1 (above) were used to amplify the mdeA1 segment, again with the 3' end of mdePr1-1 and mdePr1-6 overlapping the 5' end of the template, and each 3' end (of oligonucleotide or template) priming the extension of the full length segment product. Similarly, mdePr2-1 (86 pmoles), mdePr2-6 (86 pmoles), and 1 µl template tpA2; mdePr3-1 (74 mdePr3-6

(84 pmoles), and 1 µl tpA3 were used to amplify mdeA2 and mdeA3 segment respectively. The PCR reaction conditions were as follows: first denaturation at 94° C. for 2 min; then 25 cycles of denaturation at 94° C. for 30 sec, annealing at 51° C. for 40 sec, and extension at 72° C. for 30 sec; followed by a final extension at 72° C. for 7 min.

The PCR-amplified products were identified by size on the 2% agarose gel, a 441 bp-band for mdeA1, a 430 bp-band for mdeA2, and a 383 bp-band for mdeA3. The DNAs from the bands were extracted by using QIAquick gel extraction kit.

EXAMPLE 3

Cloning the Synthetic DNA Fragments mdeA1, mdeA2, and mdeA3 Into an Appropriate Vector The vector pGEM-5Z (Promega, 3003 bps), and the purified PCR mdeA1DNA were double cut with Nco I and Pst I; pGEM-3Z (Promega, 2743 bps), and the purified PCR mdeA2 DNA were double cut with Pst I and EcoR I restriction enzymes; pGEM-3Z and purified PCR mdeA3 DNA were double cut with EcoR I and BamH I restriction enzymes. These vectors carry the multiple cloning site arrangement from pUC18, and are ampicillin resistant. All restriction digestion reactions were incubated overnight at 37° C. The digested products were then purified by gel electrophoresis on a 2% agarose gel followed by extraction of the DNA using a QIAquick gel extraction kit.

The purified, double cut pGEM-5Z and mdeA1 were ligated with T4 DNA ligase and buffers (NEB) and incubated overnight at 16° C. Similarly, the double cut pGEM-3z and mdeA2, and double cut pGEM-3z and mdeA3, were ligated with T4 DNA ligase, but they were incubated at 12° C. because EcoR I site requires lower temperature to anneal. Several reactions were carried out for each construct to ensure optimization of molar ratios between vector and insert (e.g. 1:1, 1:3, and 3:1 vector:insert ratio). FIG. 3 illustrates the multiple cloning site and ligation of inserts into the vectors.

E. coli JM109 competent cells (Promega or Bio 101) were transformed with the ligation reactions described above using a standard heat shock transformation procedure (Sambrook et al., 1989, supra). To select for colonies containing mdeA1, mdeA2, and mdeA3 clones, the cells were grown on LB+Ampicillin (50 µg/µl) plates.

Transformant colonies were first tested with PCR screening using the mdePr1-1, mdePr1-6, mdePr2-1, mdePr2-6, mdePr3-1, and mdePr3-6 as the primers for mdeA1, mdeA2, and clones respectively. The PCR reaction volume was 25 µl with 0.2 mM dNTPs and 20 pmoles of each primers. The templates were picked directly from the colonies, and the conditions were as follows: first denaturation at 94° C. for 4 min; then 25 cycles of denaturation at 94° C. for 30 s; annealing at 57° C. for 40 s; and extension at 72° C. for 30 s; then a final extension at 72° C. for 7 min. The positive colonies containing mdeA1, mdeA2, or mdeA3 clones were identified by the presence of 441 bp, 430 bp, or 383 bp bands respectively.

To further confirm that the colony actually carried the mdeA1, mdeA2, or mdeA3 construct, restriction mapping of its plasmid was done by cutting the plasmid with Nco I+Pst I, Pst I+EcoR I, or EcoR I+BamH I. The presence of a 426 bp-band (mdeA1), a 414 bp-band (mdeA2), or a 367 bp-band (mdeA3) would be expected on 2% agarose gel if the plasmid carries the proper insert.

EXAMPLE 4

Sequencing of the Synthetic mdeA1, mdeA2, and mdeA3 DNA Fragments

After isolating plasmids containing the mdeA1, mdeA2 and mdeA3 inserts, the clones were submitted to the UCLA sequencing facility (Los Angeles, Calif.) for sequencing. M13 forward and reverse primers were used. Clones that carried the correct DNA sequence of mdeA1, mdeA2, and mdeA3 were selected and named pSmA1-17, pSmA2-8, and pSmA3-3.

EXAMPLE 5

Construction of Full-length synmdeA Encoding Methionine Gamma-lyase

The colonies containing pSmA1-17, pSmA2-8, and pSmA3-3 were cultured with LB+ampicillin (50 µg/µl) overnight at 37° C. Plasmids were extracted using QIAprep spin miniprep kit (QIAGEN, Inc., Valencia, Calif.). The plasmids pSmA1-17, pSmA2-8, and pSmA3-3 were double cut overnight at 37° C. with Nco I/Pst I, Pst I/EcoR I, and EcoR I/BamH I restriction enzymes respectively. A pET15b vector (Novagen) was cut with Nco I/BamH I restriction enzymes, and a pBAD/His C vector (Invitrogen) was cut with Nco I/Bgl II. The double cut DNAs were separated on 2% agarose gel, and the bands corresponding to mdeA1 (426 bps), mdeA2 (414 bps), mdeA3 (367 bps), pET15b (5 k bps), and pBAD/His C (4 kbs) were isolated and purified using QIAquick gel extraction kit.

Purified mdeA1, mdeA2, and mdeA3 DNAs were then ligated into double cut pET15b at Nco I and BamH I, or pBAD/His C at Nco I and Bgl II cloning sites using T4 DNA ligase overnight at 12° C.

The resulting plasmids were transformed into E. coli JM109 competent cells using a standard heat shock transformation procedure (Sambrook et al., 1989, supra). To select the positive clones containing synmdeA, the cells were grown on LB+Ampicillin (501 µg/µl) plates overnight at 37° C.

The transformant colonies were first checked with the PCR screening method described above by using mdePr1-1 and mdePr3-6 as the primer probes. A 1200 bp-band was expected on the agarose gel if the colony contained synmdeA clones. Selected pET15b and pBAD/His C vectors carrying the synmdeA insert were named pTM-1 and pBM-1 overexpression plasmids, respectively. The PCR positive colonies were then further confirmed by using a restriction mapping method, with Nco I and BamH I restriction enzymes used on pTM-1, and Nco I and Hind III restriction enzymes used on pBM-1. Again, 1200 bp-bands were seen on 2% agarose gels.

Plasmids pTM-1 and pBM-1 were transferred to expression host E. coli BL21(DE3) and LMG 194 by first plasmid extraction, followed by transformation.

EXAMPLE 6

Over-expression of Synthetic L-Methionine-alpha-gamma-lyase Gene

Host E. coli strains carrying pTM-1 and pBM-1, referred to as BL/pTM01 and LMG/pBM01 respectively, were grown on LB+ampicillin plate and RMG+ampicillin plate respectively. A single colony from each plate was then picked and cultured overnight in LB+ampicillin liquid medium. Then 5 ml of LB+ampicillin was inoculated with 100 µl of each overnight culture, and each was incubated for 2 hours at 37° C. with shaking or until O.D.$_{600}$ (nm) reached 0.8–0.9. Initially, 1 ml of each culture was removed as a non-induced control. BL/pTM01 culture was then induced to express protein by adding IPTG to a final concentration of 2 mM, and LMG/pBM01 culture was induced with a final concentration of 0.02% L-arabinose. Incubation was continued at 37° C. for 3 hours. Samples of 1 ml were collected every hour. All samples were centrifuged at 12,000×g for 3 minutes. The cells were then lysed by resuspension in 1×NuPAGE sample buffer (Novex) containing 50 mM DTT, and incubation at 97° C. for 3 minutes. After centrifugation for 10 min at 12,000×g, the supernatants were separated along with protein size markers by SDS-page on 4%–20% gradient polyacrylamide gel (NuPAGE MES SDS, Novex) for 1 hour at 150 volts. The gels were stained by Coomassie blue for 2 hours and destained in 10% acetic acid, 20% methanol solution, followed by destaining in 7% acetic acid, 5% methanol. 43 kD bands corresponding to a molecular weight marker were seen on the destained gels (FIG. 4). These bands corresponded to the major protein in the induced samples. As seen in FIG. 4, expression of synmdeA was vastly superior to expression of the native enzyme, seen in FIG. 5. The native enzyme expressed poorly in E. coli, and was a truncated portion of the complete gene. Attempted expression of the native gene gave a protein of apparent molecular weight approximately 28 kD, indicating that a substantial part of the enzyme was missing. The protein showed no methionine gamma-lyase activity. Without wishing to be bound to any particular mechanism, it is hypothesized that the truncation was caused by an interruption in translation at a rare codon. This speculation is supported by the fact that an interruption at this point would result in a polypeptide product having a molecular weight of approximately 28 kD.

EXAMPLE 7

Comparison of Native mdeA and synmdeA Gene Expression

To demonstrate the usefulness of the synthetic gene for the expression of difficult to express genes in E. coli, the synmdeA gene was expressed in E. coli using the vector pET15b. This gene encodes a methionine β lyase enzyme, but contains an additional amino acid relative to the native protein described by Soda and co-workers (e.g., U.S. Pat. No. 5,863,788). The results are shown in the gel in FIG. 4A. Based on the density of the band corresponding to the methionine-gamma lyase enzyme of approximate molecular weight 40,000 we estimate the level of expression to be 10% or more of the total protein in the crude cell lyrate of the E. coli host. By contrast, expression of the native mdeA gene in the vector pSIT is substantially less under the same induction conditions (FIG. 4B). In the experiment shown in FIG. 4B, all samples were incubated at 37 C. The induced samples contain extra bands of about 28 kD which indicate that premature termination of the enzyme occurred during translation of the native gene. Both the native and synthetic gene vectors are under the control of T7 RNA polymerase promoters.

To put these results into another context, the expression reported by Soda and coworkers in U.S. Pat. Nos. 5,861,154 and 5,863,788 is reported to be 0.82 units/mg. Using the specific activity of the purified enzyme of 20.4 units/mg reported by Soda in Anal. Biochime. 138, 421–424 (1984), the expression level is estimated to be no more than 4% of the total protein in the E. coli host. This estimate is an upper limit on the expression reported by Soda because the reported activity involves some partial purification of the enzyme prior to assay.

EXAMPLE 8

Comparison of Expression of Genes With Different $\Delta G_{folding}$

FIG. 5 is a gel showing expression of two genes with different $\Delta G_{folding}$. Naphthalene Dioxygenase from P. putida has a $\Delta G_{folding}$ of −256.1 kcal/mol. This very low free energy would not be expected, under the principles of the invention, to express well. In fact, as seen in lanes 1–4 of FIG. 5, it does not. By contrast, another gene, methionine gamma lyase (mgl 1) from T. vaginalis has a $\Delta G_{folding}$ of −152.5 kcal/mol. As can be seen from lanes 6–9 of FIG. 5, this protein can be induced and expresses well under the conditions used. Both genes were cloned into the pBAD vector and grown at 37° C.

The preceding description has been presented with references to presently preferred embodiments of the invention. Persons skilled in the art and technology to which this invention pertains will appreciate that alterations and changes in the described structures and methods can be practiced without meaningfully departing from the principle, spirit and scope of this invention.

Accordingly, the foregoing description should not be read as pertaining only to the precise structures and methods described and shown in the accompanying drawings, but rather should be read as consistent with and as support for the following claims, which are to have their fullest and fairest scope.

What is claimed is:

1. A method of making a synthetic nucleic acid sequence, the method comprising:

(a) providing a starting nucleic acid sequence;

(b) determining the predicted $\Delta G_{folding}$ of the starting nucleic acid sequence;

(c) modifying the starting nucleic acid sequence by replacing at least one codon from the starting nucleic acid sequence with a different corresponding codon to provide a modified nucleic acid sequence;

(d) determining the predicted $\Delta G_{folding}$ of the modified nucleic acid sequence;

(e) comparing the $\Delta G_{folding}$ of the modified nucleic acid sequence with the $\Delta G_{folding}$ of the starting nucleic acid sequence (f) determining whether the $\Delta G_{folding}$ of the modified nucleic acid sequence is increased relative to the $\Delta G_{folding}$ of the starting nucleic acid sequence by a desired amount;

(g) if the $\Delta G_{folding}$ of the modified nucleic acid sequence is not increased by the desired amount, further modifying the modified nucleic acid sequence by replacing at least one codon from the modified nucleic acid sequence with a different corresponding codon to provide a different modified nucleic acid sequence; and repeating steps (f) and (g) until the $\Delta G_{folding}$ of the modified nucleic acid sequence is increased by the desired amount to ultimately provide a final nucleic acid sequence.

2. The method of claim 1 wherein the starting nucleic acid sequence encodes an amino acid sequence.

3. The method of claim 1 further comprising physically creating the final nucleic acid sequence.

4. The method of claim 1 wherein the codon replacement is in a region of the starting nucleic acid sequence containing secondary structure.

5. The method of claim 1 further comprising selecting a host for expressing the modified nucleic acid sequence and transforming the host with the modified sequence, wherein the host expresses the modified nucleic acid sequence better than the host would express the starting sequence if the host were transformed with the starting sequence.

6. The method of claim 5 wherein the selected host is *E. coli*.

7. The method of claim 1 wherein the different corresponding codon is a codon that occurs with higher frequency in the selected host.

8. The method of claim 1 wherein the desired amount is at least about 2%.

9. The method of claim 1 wherein the desired amount is at least about 10%.

10. The method of claim 1 wherein the desired amount is at least about 20%.

11. The method of claim 1 wherein the desired amount is at least about 30%.

12. The method of claim 1 wherein the different corresponding codon has fewer guanine or cytosine residues than the replaced codon.

13. The method of claim 1 further comprising selecting a host for expressing the modified nucleic acid sequence, wherein the starting nucleic acid sequence is derived from an amino acid sequence native to a bacterium different from the host selected for expression.

14. The method of claim 13 wherein the amino acid sequence is native to a bacterium of the genus Pseudomonas.

15. The method of claim 1 wherein the starting nucleic acid sequence is a naturally occurring sequence.

16. The method of claim 1 wherein the starting nucleic acid sequence is a non- naturally occurring sequence.

17. The method of claim 1 wherein the $\Delta G_{folding}$ of the modified nucleic acid sequence is more positive than about −0.2 kcal/(mol)(base).

18. The method of claim 1 further comprising selecting a desired amino acid sequence, wherein the modified nucleic acid sequence encodes the desired amino acid sequence.

19. The method of claim 18 further comprising selecting a host for expressing the desired amino acid sequence, wherein the host is an enteric bacterium, the amino acid sequence is native to a bacterium different from the host selected for expression, and the different corresponding codon is one which occurs with higher frequency in the enteric bacterium than does the replaced codon.

20. The method of claim 19 wherein the enteric bacterium is *Escherichia coli*.

21. The method of claim 19 wherein the amino acid sequence is native to a bacterium of the genus Pseudomonas.

22. The method of claim 1 wherein the modified, final sequence is more amplifiable than the starting sequence.

23. The method of claim 1 wherein the different codon is selected from the most frequently used by a selected host.

* * * * *